United States Patent
Westenfelder, II et al.

(10) Patent No.: US 11,680,697 B2
(45) Date of Patent: Jun. 20, 2023

(54) LIGHT HEAD WITH ROTATING LENS ASSEMBLY AND METHOD OF OPERATING SAME

(71) Applicant: American Sterilizer Company, Mentor, OH (US)

(72) Inventors: David A. Westenfelder, II, Mantua, OH (US); Jill A. Sanders, Cleveland, OH (US)

(73) Assignee: American Sterilizer Company, Mentor, OH (US)

( * ) Notice: Subject to any disclaimer, the term of this patent is extended or adjusted under 35 U.S.C. 154(b) by 0 days.

(21) Appl. No.: 17/151,760

(22) Filed: Jan. 19, 2021

(65) Prior Publication Data
US 2021/0239299 A1    Aug. 5, 2021

Related U.S. Application Data

(60) Provisional application No. 62/968,196, filed on Jan. 31, 2020.

(51) Int. Cl.
*F21V 14/06* (2006.01)
*A61B 90/35* (2016.01)
(Continued)

(52) U.S. Cl.
CPC .............. *F21V 14/06* (2013.01); *A61B 90/30* (2016.02); *A61B 90/35* (2016.02); *F21V 5/02* (2013.01);
(Continued)

(58) Field of Classification Search
CPC ........ F21V 21/40; F21V 21/403; F21V 14/06; F21V 14/065; F21V 17/005;
(Continued)

(56) References Cited

U.S. PATENT DOCUMENTS 3,887,801 A  *  6/1975  Ilzig ........................ F21V 19/02
                                                    362/233
4,037,096 A  *  7/1977  Brendgord ............ F21V 7/0008
                                                    362/294
(Continued)

FOREIGN PATENT DOCUMENTS

DE         1034116 B      7/1958
EP         2503231 A2 *   9/2012     ............... B65D 1/40
(Continued)

OTHER PUBLICATIONS

Second Written Opinion of the International Preliminary Examining Authority for corresponding PCT International Application PCT/US2021/013862 dated Dec. 12, 2021.
(Continued)

*Primary Examiner* — Jong-Suk (James) Lee
*Assistant Examiner* — James M Endo
(74) *Attorney, Agent, or Firm* — Renner, Otto, Boisselle & Sklar, LLP

(57) ABSTRACT

A light head for a medical device support system. The light head includes a housing base, an annular shape first lens, a housing cover, and a motion transfer member. The housing cover includes a cavity within which the annular shape first lens is rotatable about a rotation axis. The housing cover includes a second lens. The annular shape first lens and the second lens are in a light emitting path of the plurality of light emitting elements. The motion transfer member is configured to movably interact with a boss of the annular shape first lens to rotate the annular shape first lens about the rotation axis and within the cavity. A periphery of the annular shape first lens includes guide members configured to position the boss of the annular shape first lens to movably interact with the motion transfer member.

27 Claims, 26 Drawing Sheets

(51) Int. Cl.
*F21V 5/04* (2006.01)
*F21V 17/00* (2006.01)
*F21V 5/02* (2006.01)
*A61B 90/30* (2016.01)
*F21W 131/205* (2006.01)

(52) U.S. Cl.
CPC ............ *F21V 5/046* (2013.01); *F21V 17/005* (2013.01); *A61B 2090/308* (2016.02); *F21W 2131/205* (2013.01)

(58) Field of Classification Search
CPC ........ F21V 17/104; F21V 17/02; F21V 5/046; F21W 2131/20; F21W 2131/202; F21W 2131/205; A61B 90/35; A61B 2090/308; F21Y 2105/18; F21S 10/007
See application file for complete search history.

(56) References Cited

U.S. PATENT DOCUMENTS

| | | | | |
|---|---|---|---|---|
| 4,316,237 | A * | 2/1982 | Yamada | F21V 21/14 362/372 |
| 4,928,211 | A * | 5/1990 | Hallings | F21V 21/30 362/804 |
| 4,994,945 | A * | 2/1991 | O'Shea | F21V 5/02 362/268 |
| 5,128,848 | A | 7/1992 | Enders et al. | |
| 5,485,319 | A * | 1/1996 | Lemons | G02B 5/045 359/833 |
| 5,951,139 | A | 9/1999 | Smith et al. | |
| 8,454,197 | B2 | 6/2013 | Hauschulte et al. | |
| 9,470,382 | B1 * | 10/2016 | Sharrah | H05B 45/10 |
| 9,470,405 | B2 * | 10/2016 | Boccoleri | F21V 21/40 |
| 2002/0089857 | A1 * | 7/2002 | Borders | F21V 14/02 362/399 |
| 2002/0172033 | A1 * | 11/2002 | Bulko | F21V 7/24 362/293 |
| 2003/0165055 | A1 * | 9/2003 | Scholz | F21V 21/403 362/276 |
| 2007/0041167 | A1 * | 2/2007 | Nachi | F21V 29/773 362/241 |
| 2007/0236931 | A1 * | 10/2007 | Chien | F21V 21/08 362/249.07 |
| 2008/0304281 | A1 * | 12/2008 | Scholz | F21V 14/06 362/572 |
| 2010/0121154 | A1 * | 5/2010 | Kusner | F21S 41/55 600/249 |
| 2012/0043915 | A1 * | 2/2012 | Rohwedder | F21V 21/40 362/271 |
| 2012/0075832 | A1 * | 3/2012 | Schmid | F21V 21/403 362/33 |
| 2013/0107513 | A1 * | 5/2013 | Lundberg | F21V 14/06 362/231 |
| 2015/0276176 | A1 * | 10/2015 | Ju | F21V 9/08 362/277 |
| 2017/0130932 | A1 * | 5/2017 | Longoni | F21V 7/048 |
| 2017/0296291 | A1 | 10/2017 | Barlund | |

FOREIGN PATENT DOCUMENTS

| | | | | |
|---|---|---|---|---|
| EP | 3081856 | A1 | 10/2016 | |
| EP | 3081857 | A1 * | 10/2016 | ............ A61B 90/30 |
| EP | 3343099 | A1 | 7/2018 | |
| WO | 2012156617 | A1 | 11/2012 | |
| WO | 2016101491 | A1 | 6/2016 | |

OTHER PUBLICATIONS

International Search Report and Written Opinion for corresponding PCT International Application PCT/US2021/013862 dated May 11, 2021.

Skytron; Aurora Four Surgical Light; Product Brochure; Webpage first available Jun. 15, 2016 (archive.org).

Daray Medical; SL400 Range LED Operating Theatre Light; User Manuel and Installation Guide; Webpage accessed Jul. 11, 2019 (not archived on archive.org).

* cited by examiner

LIGHT HEAD WITH ROTATING LENS ASSEMBLY AND METHOD OF OPERATING SAME

This application claims priority to U.S. Patent Application No. 62/968,196 filed Jan. 31, 2020, the entire disclosure of which is hereby incorporated by reference.

FIELD OF INVENTION

This application relates generally to a light head for a medical device support system or carry system and a method of operating such a light head, and more particularly to a light head that has a rotating lens assembly provided within limited space constraints and a method of operating such a light head.

BACKGROUND

Light heads for medical device support systems, suspension systems and/or other carry systems, are used in health treatment settings such as hospital examination rooms, clinics, surgery rooms and emergency rooms to illuminate a surgical treatment site or other medical site below the light heads. The light heads typically include a housing, one or more light emitting elements mounted inside the housing, one or more lenses through which light emitted by the light emitting elements is transmitted to the surgical site, and a handle mounted to the housing to enable a healthcare professional to adjust the position of the light head according to the needs of a specific medical procedure.

For light heads in some medical device support systems or carry systems, there remain various shortcomings, drawbacks, and disadvantages relative to certain applications. Some applications require that the light head provide a means for controlling light emission attributes such as light field size, light distribution, and central illuminance. This typically is accomplished by control elements integrated into the light head housing, handle, or support structure, and/or by rotation of the handle relative to the light head housing. For example, the control elements may control the intensity of the light emitting elements and handle rotation may control relative positioning of the lenses to alter field diameter or light distribution. In any event, this improved functionality and flexibility in illumination control has led to increasingly more complex light head structures and componentry and in some cases a corresponding increase in size and weight of the light head.

On the other hand, healthcare professionals also prefer reduced overall size and lower height light heads in the operating theater. Smaller size light heads can more easily be maneuvered and adjusted. A lower profile can aid in reducing impairments to laminar flow within the operating theater and is also more aesthetically appealing. The drawback to smaller size light heads, however, is that their reduced volume results in space constraints that are oftentimes incompatible with solutions designed to improve functionality.

Accordingly, there remains a need for further contributions in this area of technology.

SUMMARY OF INVENTION

According to one aspect of the invention, a light head for a medical device support system includes a housing base, a housing cover, an annular shape lens, and a motion transfer member. The housing base includes a plurality of light emitting elements. The annular shape first lens has a rotation axis. The housing cover includes a cavity within which the annular shape first lens is rotatable about the rotation axis. The housing cover includes a second lens. The annular shape first lens and the second lens are in a light emitting path of the plurality of light emitting elements. The motion transfer member is configured to movably interact with a boss of the annular shape first lens to rotate the annular shape first lens about the rotation axis and within the cavity. A periphery of the annular shape first lens includes guide members configured to position the boss of the annular shape first lens to movably interact with the motion transfer member.

Embodiments of the invention may include one or more of the following additional features separately or in combination.

The light head may further include a plurality of collimators in the light emitting path of the plurality of light emitting elements.

The guide members may be located at at least one of an inner periphery and an outer periphery of the annular shape first lens and may be configured to slidably contact a bearing surface of the housing cover.

The bearing surface of the housing cover may guide the guide members of the annular shape lens to guide the annular shape lens in a concentric relationship with an annular shape outer cover of the housing cover.

The guide members may include radially inward tabs that protrude from an inner periphery of the annular shape first lens and may be configured to slidably contact a bearing surface of the housing cover.

The guide members may include radially outward tabs that protrude from an outer periphery of the annular shape first lens and may be configured to slidably contact a bearing surface of the housing cover.

The annular shape first lens and the boss may be a single integral monolithic structure.

The annular shape first lens and the boss may be a single integral molded component.

The rotation axis may be at the center of the annular shape first lens.

The motion transfer member may include a lever.

The housing cover may include within the cavity thereof at least one of an inner periphery lower wall and an outer periphery lower wall, wherein the annular shape first lens and housing cover are arranged so that the annular shape first lens is slidably movable on the at least one of the inner periphery lower wall and the outer periphery lower wall.

The housing cover and the at least one of the inner periphery lower wall and the outer periphery lower wall may be a single integral molded component.

The housing cover may include a plurality of lens restricting members situated within the cavity of the housing cover and attached to one or more surfaces of the housing cover.

The annular shape first lens may be radially restricted by bearing surfaces of the respective plurality of lens restricting members to rotationally guide the annular shape first lens about the rotation axis and within the cavity of the housing.

The annular shape first lens may be axially restricted between bearing surfaces of the respective plurality of lens restricting members and bearing surfaces of the housing cover to rotationally guide the annular shape first lens about the rotation axis and within the cavity of the housing.

The plurality of lens restricting members may be attached to the surface of the housing cover by fasteners.

According to another aspect of the invention, a light head for a medical device support system includes a housing base, an annular shape first lens, a housing cover, a lever, and a driving source. The housing base includes a plurality of light emitting elements. The annular shape first lens has a rotation axis. The housing cover includes a cavity within which the annular shape first lens is rotatable about the rotation axis. The housing cover includes a second lens. The annular shape first lens and the second lens are in a light emitting path of the plurality of light emitting elements. The lever is movable relative to a fulcrum of the light head. The lever includes a first end and a second end at opposite sides of the fulcrum, the first end spaced a first distance from the fulcrum, the second end spaced a second distance from the fulcrum. The lever is configured to transfer motion from the driving source at the first end thereof into rotational motion of the annular shape first lens about the rotation axis and within the cavity at the second end thereof in response to movement of the lever relative to the fulcrum based on the ratio of the first distance from the fulcrum to the second distance from the fulcrum.

The driving source includes a handle rotatably mounted coaxially to a hub of the light head, and the lever is configured to transfer rotational motion of the handle at the first end of the lever into rotational motion of the annular shape first lens at the second end of the lever.

The fulcrum may include a round shape fastener secured via a bracket to the hub.

The first end of the lever may be movably coupled to a bushing of the handle.

The hub may be secured to the housing cover.

The second end of the lever may be movably coupled to the annular shape first lens.

The cavity may have a predetermined depth and the entire lever may be configured to move relative to the fulcrum within the depth of the cavity.

The first end, the fulcrum, and the second end may be arranged at respective first, second, and third radial distances from the rotation axis, wherein the third radial distance is greater than the second radial distance, and the second radial distance is greater than the first radial distance.

According to another aspect of the invention, a method of operating a light head of a medical device support system is provided, including providing a light head including: a housing base including a plurality of light emitting elements; an annular shape first lens that has a rotation axis; a housing cover including a cavity within which the annular shape first lens is rotatable about the rotation axis, wherein the housing cover includes a second lens; wherein the annular shape first lens and the second lens are in a light emitting path of the plurality of light emitting elements; movably interacting a motion transfer member with a boss of the annular shape first lens to rotate the annular shape first lens about the rotation axis and within the cavity; configuring guide members located at a periphery of the annular shape first lens to position the boss of the annular shape first lens to movably interact with the motion transfer member.

According to another aspect of the invention, a method of operating a light head of a medical device support system includes providing a light head including: a housing base including a plurality of light emitting elements; an annular shape first lens that has a rotation axis; a housing cover including a cavity within which the annular shape first lens is rotatable about the rotation axis, wherein the housing cover includes a second lens; wherein the annular shape first lens and the second lens are in a light emitting path of the plurality of light emitting elements; a driving source; moving a lever relative to a fulcrum of the light head, wherein the lever includes a first end and a second end at opposite sides of the fulcrum, the first end spaced a first distance from the fulcrum, the second end spaced a second distance from the fulcrum; transferring motion from the driving source at the first end of the lever into rotational motion of the annular shape first lens about the rotation axis and within the cavity at the second end of the lever in response to movement of the lever relative to the fulcrum based on the ratio of the first distance from the fulcrum to the second distance from the fulcrum.

The following description and the annexed drawings set forth certain illustrative embodiments of the invention. These embodiments are indicative, however, of but a few of the various ways in which the principles of the invention may be employed. Other objects, advantages and novel features according to aspects of the invention will become apparent from the following detailed description when considered in conjunction with the drawings.

BRIEF DESCRIPTION OF THE DRAWINGS

The annexed drawings, which are not necessarily to scale, show various aspects of the invention.

DETAILED DESCRIPTION

Figure 1:
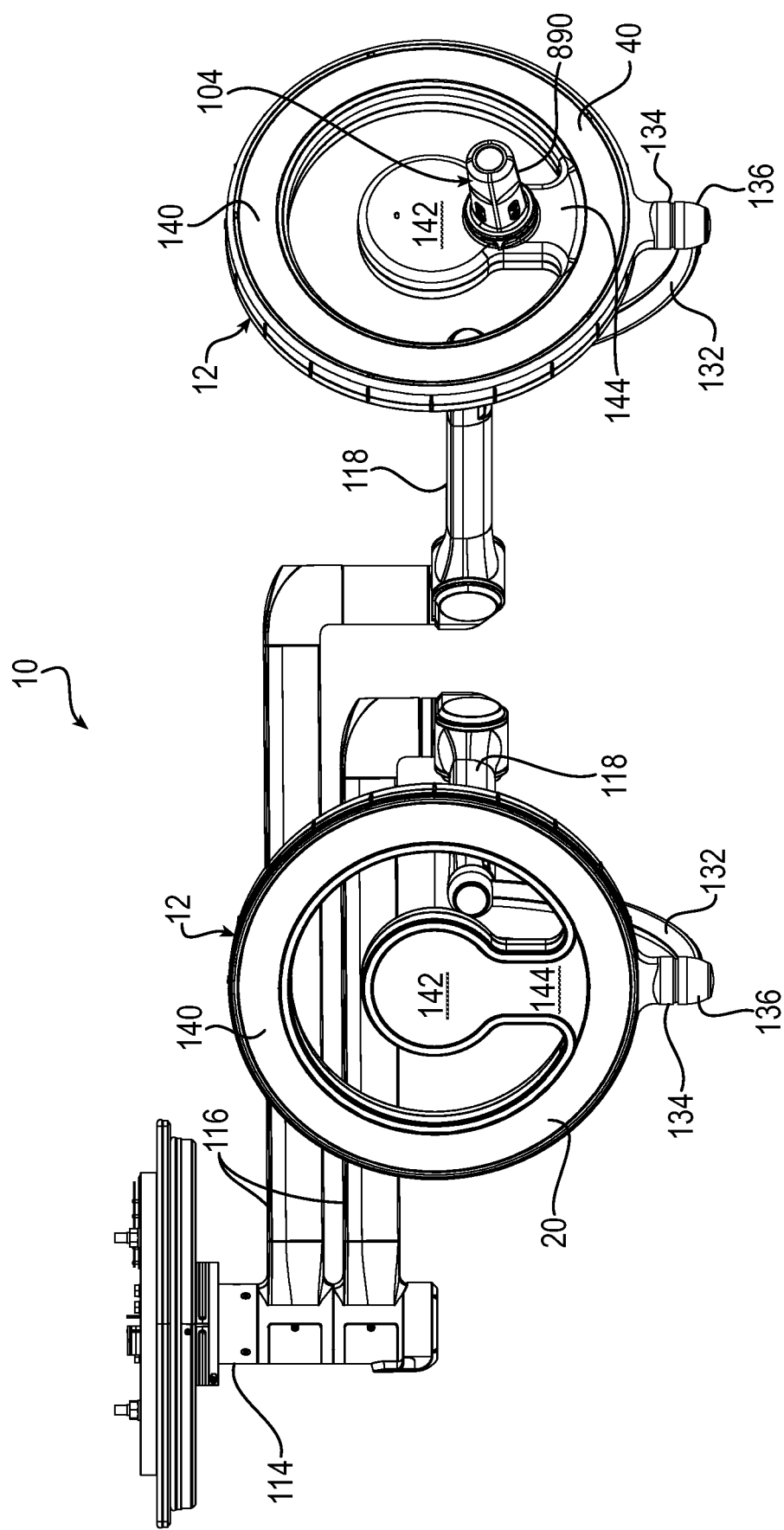
FIG. 1 is a side elevation view of an overall configuration of a medical device support system in accordance with an embodiment of the invention, showing a top of a left positioned light head and a bottom a right positioned light head.

While the present invention can take many different forms, for the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications of the described embodiments, and any further applications of the principles of the invention as described herein, are contemplated as would normally occur to one skilled in the art to which the invention relates.

FIGS. 1-6 show a medical device support system 10 including two light heads 12 in accordance with an embodiment of the invention. Each light head 12 of the system 10 includes a housing base 20, a plurality of light emitting elements 24, an annular shape lens 30, a housing cover 40 including a housing lens 46, and a motion transfer member 50 which may include a lever, gear arrangement, or articulating assembly. The annular shape lens 30 and the housing lens 46 are in a light emitting path LP of the plurality of light emitting elements 24. With reference to FIGS. 2-6, and as will be described in greater detail below, within a small structural envelope the motion transfer member 50 is configured to movably interact with a boss 62 of the annular shape lens 30 to rotate the annular shape lens 30 about a rotation axis A-A and within a cavity 70 of the housing cover 40 while guide members 84, 88 at a periphery of the annular shape lens 30 position the boss 62 to movably interact with the motion transfer member 50. As will also be described herein, and briefly referring to FIGS. 2-4 and 7, the motion transfer member 50 may be movably coupled to a driving source 104, such as a handle, of the light head 12 such that motion from the driving source 104 translates into rotation of the annular shape lens 30 about the rotation axis A-A; this also being provided within a low overall height structure advantageous for maneuverability of the light head 12 and a structure providing improved laminar flow conditions.

Turning initially then to FIG. 1, the medical device support system 10 includes a central shaft or support column 114 that is suspended from the ceiling, and two generally horizontal extension arms 116 mounted to the shaft 114 for rotational movement about the shaft 114. The central shaft 114 could be mounted to a wall or stand rather than the ceiling. Two load balancing arms 118 are pivotably mounted to the distal ends of the respective extension arms 116. The distal ends of the load balancing arms 118 are configured with yoke assemblies 132 which, in turn, support the respective light heads 12 for multi-axis movement relative to the load balancing arms 118. Each light head 12 includes a bushing or other coupling member 134 that rotatably connects the light head 12 to the distal end of an arm 136 of a respective yoke assembly 132, as shown. The load balancing arms 118 and yoke assemblies 132 enable positioning of the light heads 12 to a proper orientation relative to for example a patient operating table and healthcare professionals in the operating room.

Figure 2:
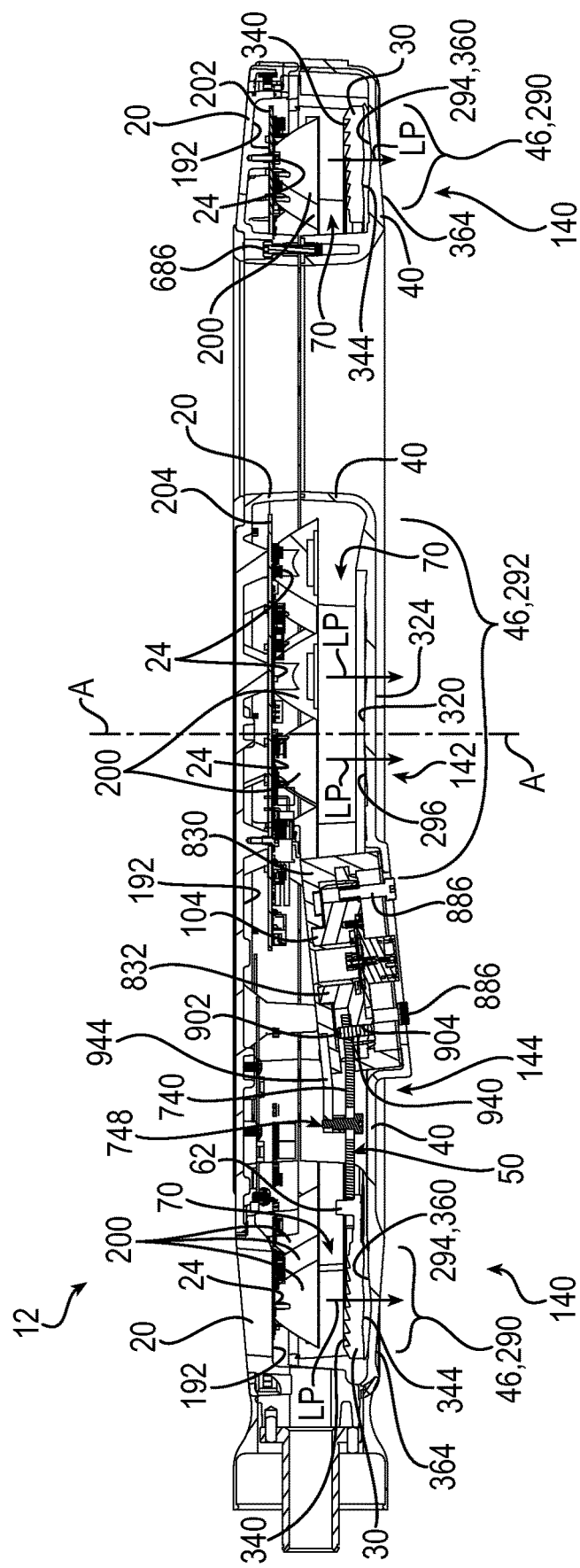
FIG. 2 is a side cross section view of a light head in accordance with an embodiment of the invention, showing a housing base, a housing cover, and internal components of the light head.
Figure 3:
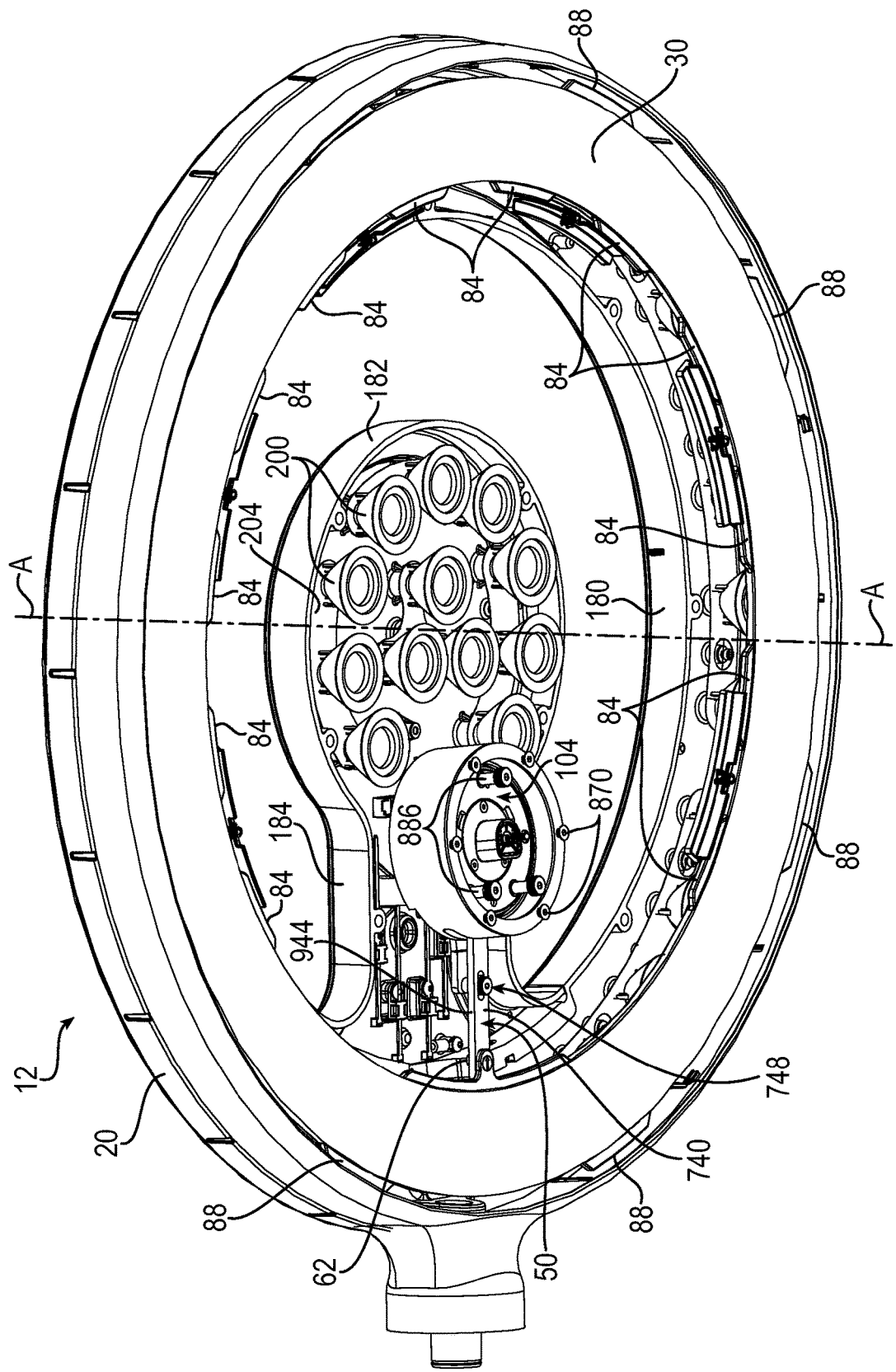
FIG. 3 is a bottom perspective view of the light head with a housing cover and handle omitted to show internal components of the light head.

As shown in FIGS. 1 and 2, each light head 12 includes an annular shape outer portion 140, an inner round portion 142, and a radially protruding arm 144 that connects the annular shape outer portion 140 to the inner round portion 142. In the illustrative embodiment, the radially protruding arm 144 arranges the annular shape outer portion 140 and the inner round portion 142 in concentric relation to one another, and in concentric relation to the rotation axis A-A of the annular shape lens 30. The radially protruding arm 144 also houses the motion transfer member 50 and one or more components of the driving source 104, to be described in greater detail below, for driving the motion transfer member 50. A controller controls the light emitting elements 24 of the annular shape outer portion 140 and the inner round portion 142 to emit light to a surgical treatment site or other medical site below the light heads 12. It will be appreciated that the annular shape outer portion 140 and the inner round portion 142 need not be in concentric relation to one another and instead can be arranged by the protruding arm in eccentric relation to one another. It will further be appreciated that in an alternate embodiment the inner round portion 142 of the light head 12 may be omitted; and in such form, only the annular shape outer portion 140 emits light to the medical treatment site.

Figure 4:
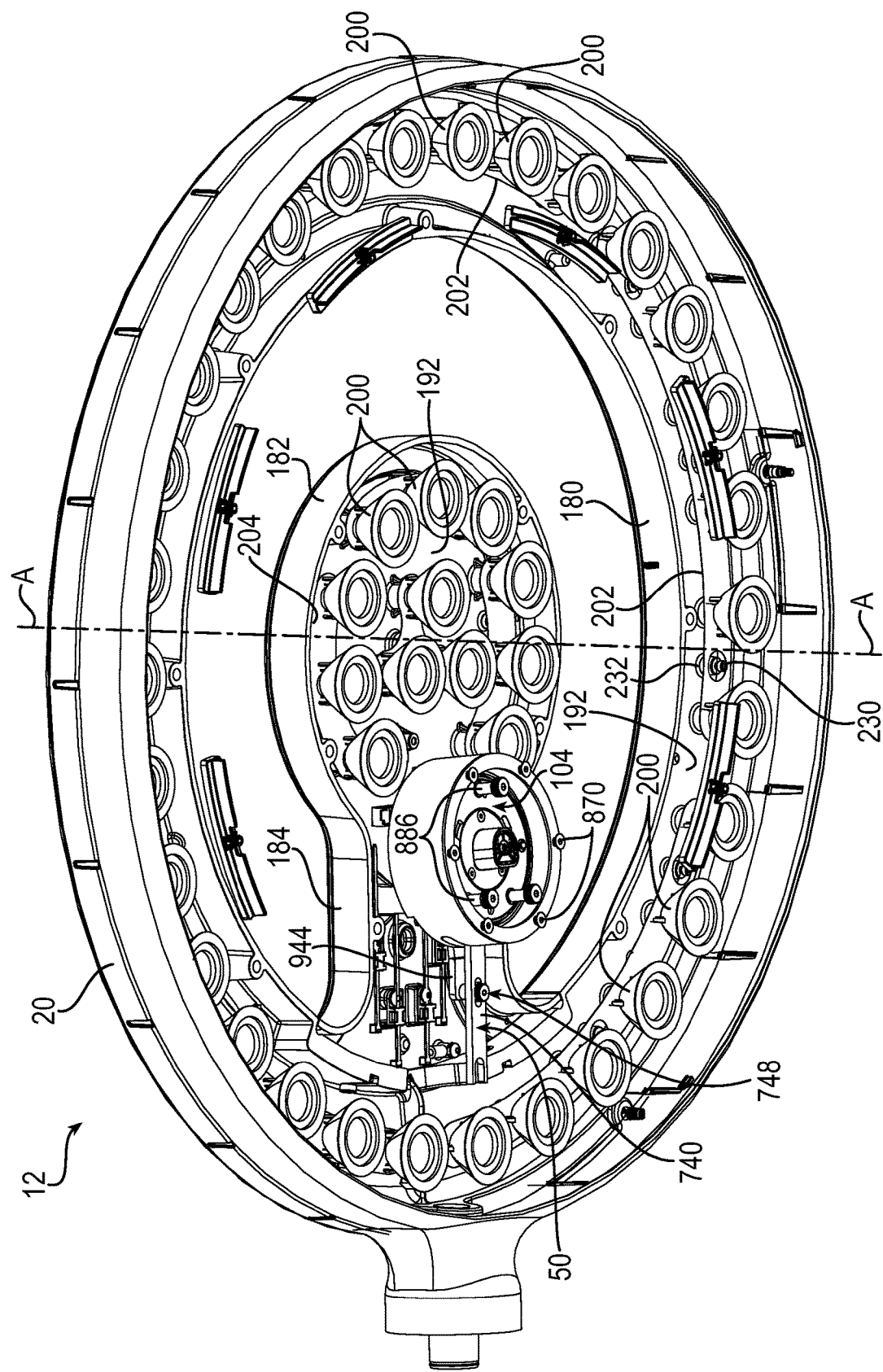
FIG. 4 is a similar view as shown in FIG. 3 except with an annular shape lens omitted to show internal components of the light head.
Figure 5:
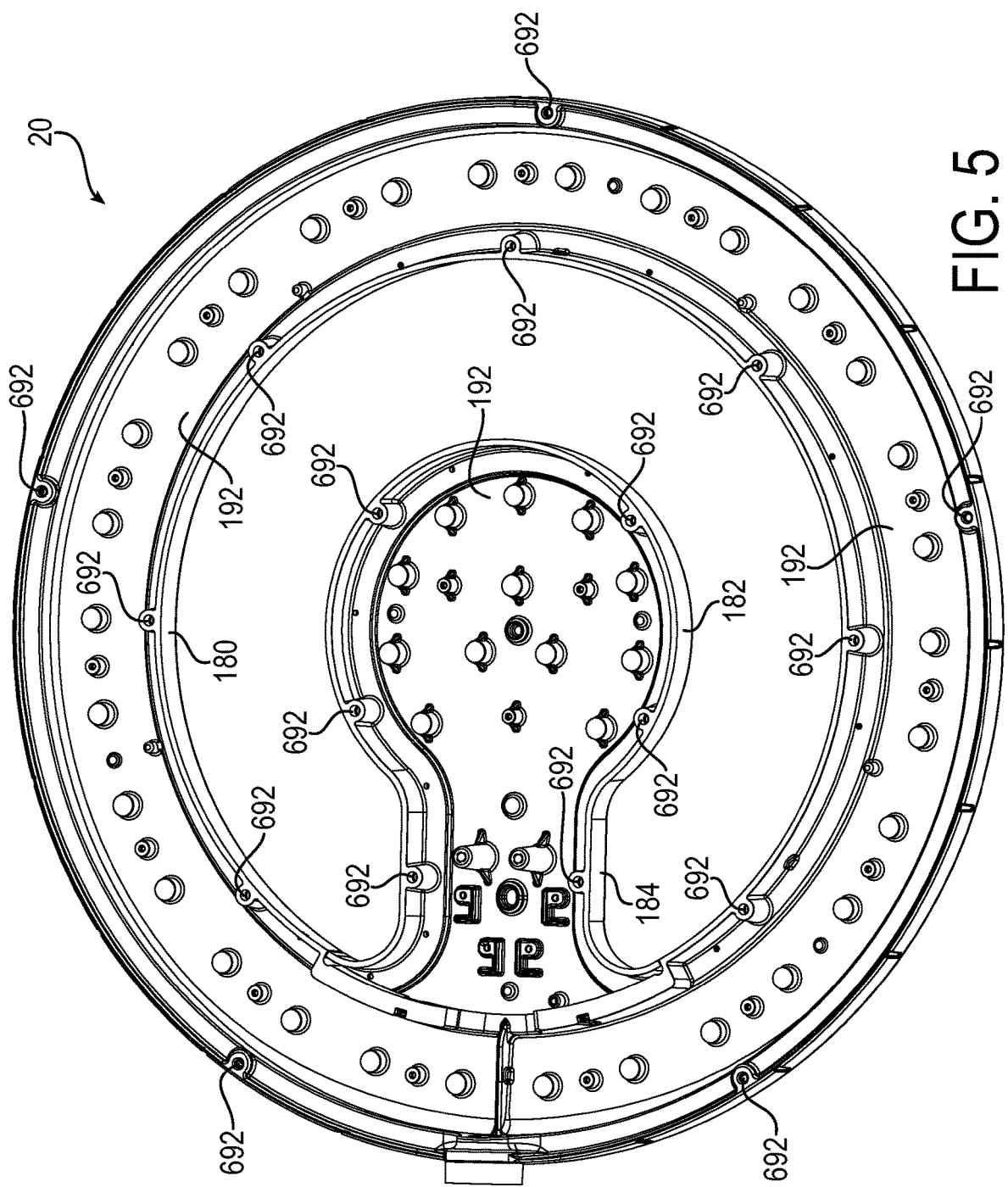
FIG. 5 is a bottom perspective view of a housing base.

FIGS. 2-6 show details of the light head 12 in accordance with an embodiment of the invention. The light head 12 includes the housing base 20 and the housing cover 40, which together define an overall form and structure of the light head 12. As shown in FIG. 5, the housing base 20 is made up of an annular shape outer base 180 and an inner round base 182 that are connected by an arm base 184 extending radially outward from the inner round base 182. The radially extending arm base 184 may also arrange the annular shape outer base 180 and the inner round base 182 in concentric relation to one another, and/or in concentric relation to the rotation axis A-A of the annular shape lens 30. In another form, the annular shape outer base 180 and the inner round base 182 may be connected by an arm base extending radially inward from the annular shape outer base 180.

Figure 9:
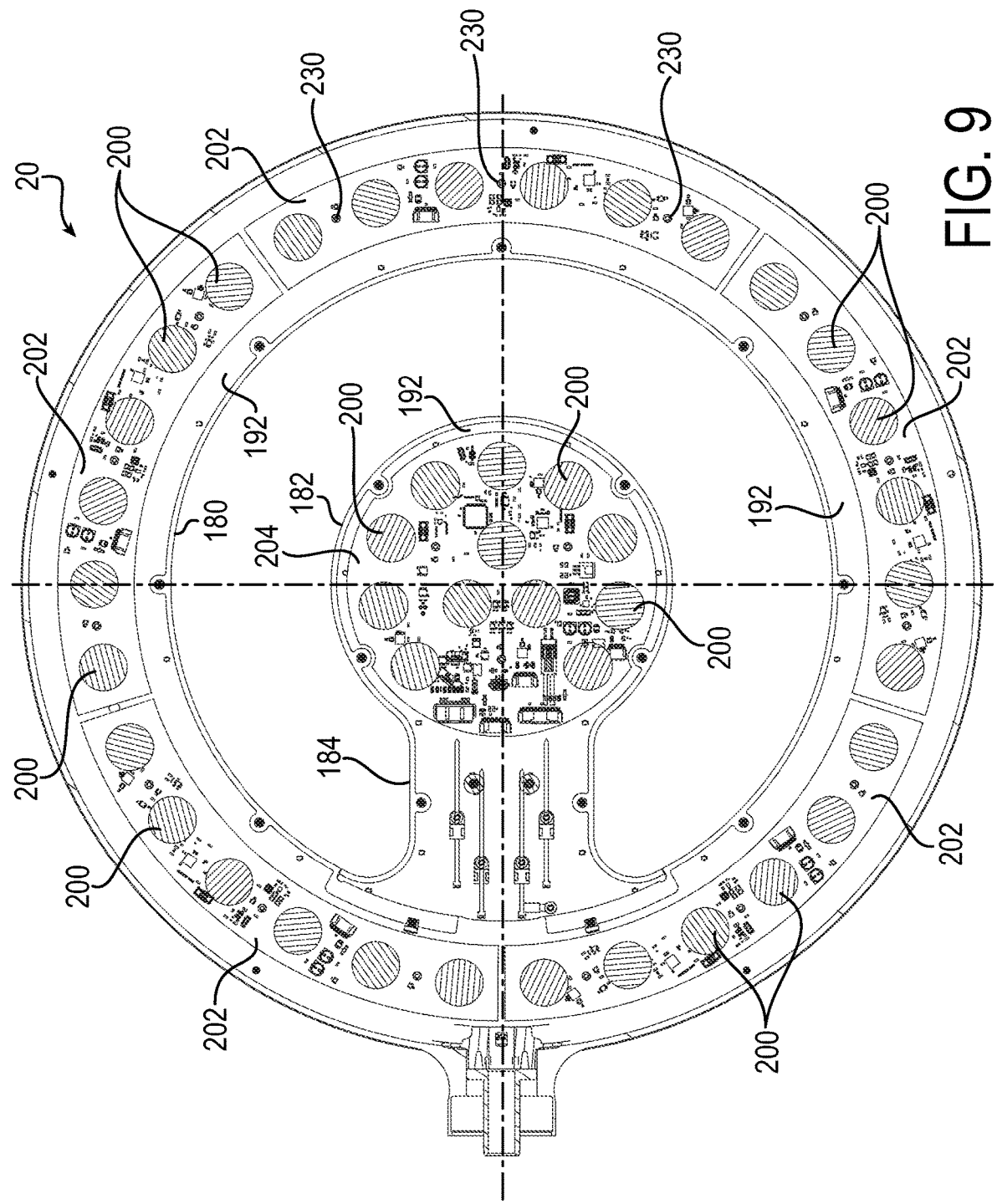
FIG. 9 is a bottom plan view of the housing base and a plurality of collimators.

An inside surface 192 of the housing base 20 supports the plurality of light emitting elements 24, which may be for example light emitting diodes (LEDs). In the illustrative embodiment, a plurality of collimators 200 are also mounted to the inside surface 192 of the housing base 20 and in the light emitting paths LP of the respective plurality of light emitting elements 24. The collimators 200 collect and direct, and/or collimate, the light into narrow beams. In one form, the collimators 200 may comprise total internal reflection (TIR) lenses. As shown in FIG. 9, the annular shape outer base 180 has 30 light emitting elements 24 and collimators 200 evenly spaced 12 degrees apart. The inner round base 182 has 12 light emitting elements 24 and collimators 200 distributed in an outer ring of nine and a triangle of three within the outer ring. Referring to FIGS. 2, 4, and 9, the light emitting elements 24 and collimators 200 may be grouped together in modules 202, 204, in the illustrative embodiment five arc shape modules 202 mounted to the inside surface 192 of the annular shape outer base 180 and one round module 204 mounted to the inside surface 192 of the inner round base 182. Referring more specifically to FIG. 9, each of the five arc shape modules 202 has six light emitting elements 24 and collimators 200, and the round inner module 204 has 12 light emitting elements 24 and collimators 200. The modules 202, 204 may be mounted to the inside surface 192 of the housing base 20 by fasteners 230 or the like threaded into corresponding risers or bosses 232 of the housing base 20.

Figure 6:
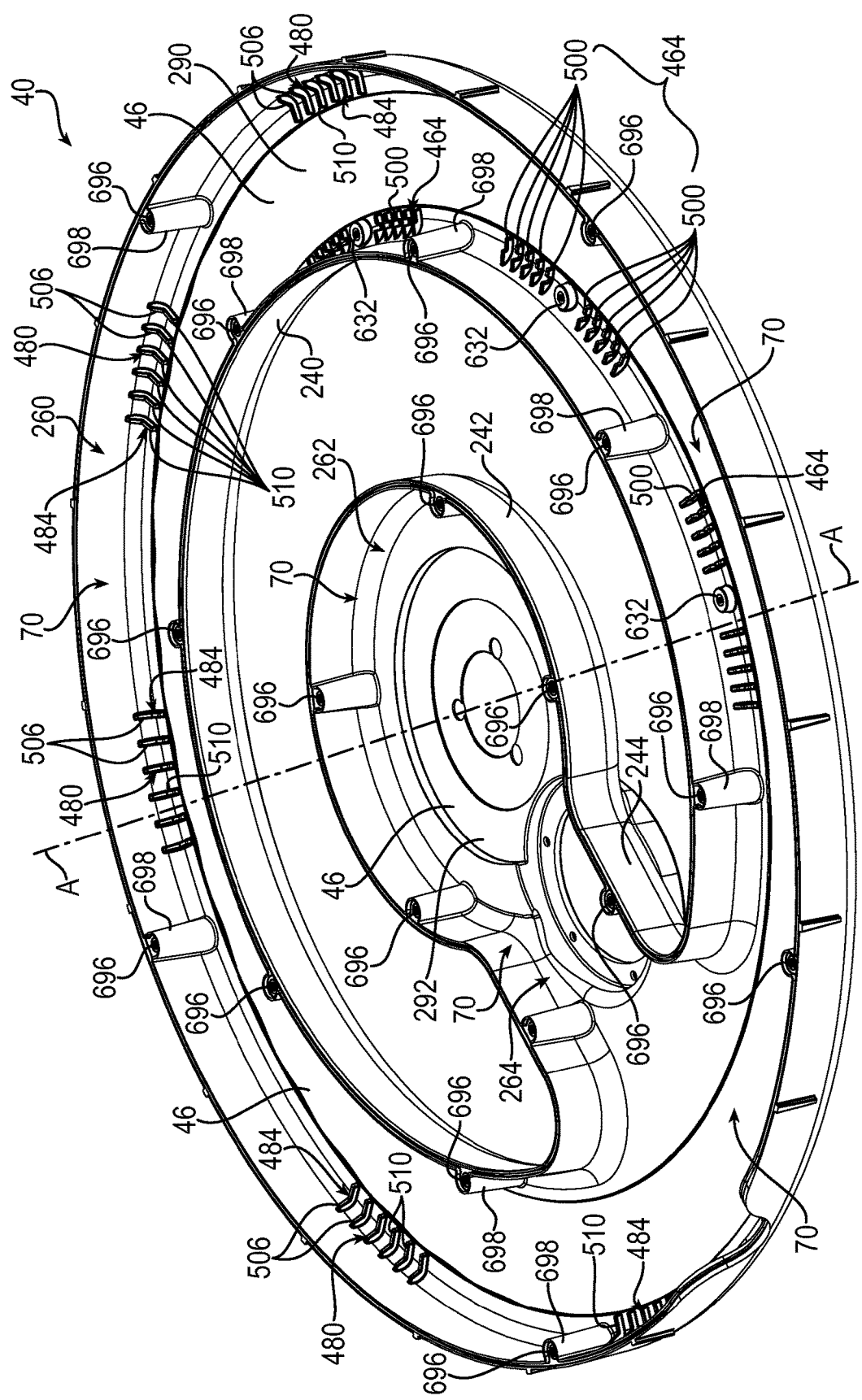
FIG. 6 is a top perspective view of a housing cover.
Figure 13:
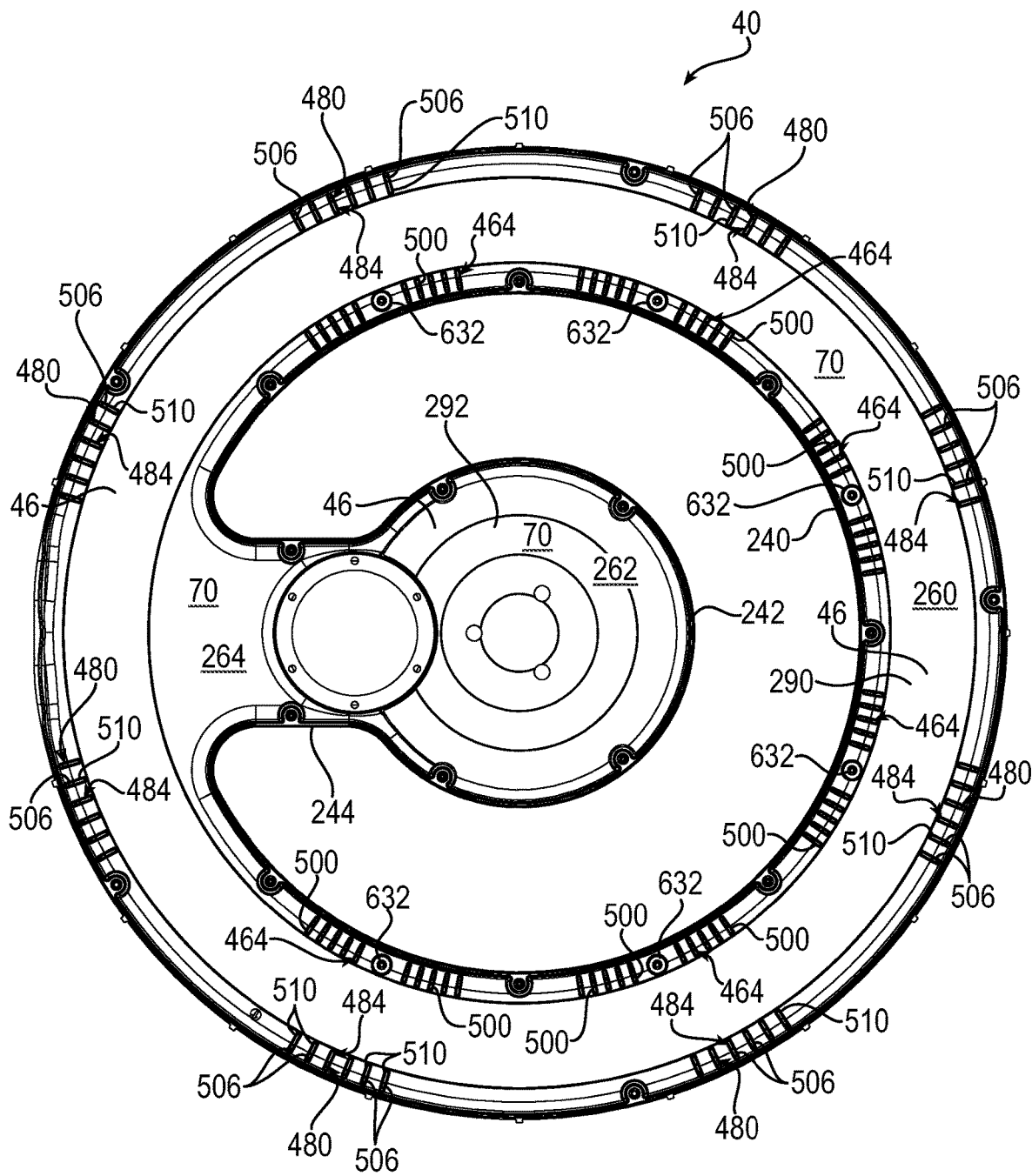
FIG. 13 is a top plan view of the housing cover.

The housing cover 40 is shown in FIGS. 6 and 13. The housing cover 40 has an annular shape outer cover 240 and an inner round cover 242 that are connected by an arm cover 244 extending radially therebetween. The radially extending arm cover 244 may also arrange the annular shape outer cover 240 and the inner round cover 242 in concentric relation to one another, and/or in concentric relation to the rotation axis A-A of the annular shape lens 30. The housing cover 40 defines a cavity 70 having three interconnected portions corresponding to the annular shape outer cover 240, the inner round cover 242, and the arm cover 244 extending radially therebetween; that is, the cavity 70 comprises an annular shape outer cavity 260, an inner round cavity 262, and a radial arm cavity 264.

The housing cover 40 also includes the housing lens 46, which in the illustrative embodiment includes an annular shape outer lens 290 and an inner round lens 292. Referring to FIGS. 2, 8, 14, and 15, the annular shape outer lens 290 forms a bottom wall 294 of the annular shape outer cover 240 and thus the bottom surface of the annular shape outer cavity 260. The inner round lens 292 forms a bottom wall 296 of the inner round cover 242 and thus the bottom surface of the inner round cavity 262. In an alternate form, the bottom wall of the annular shape outer cover 240 and/or the inner round cover 242 may be formed by a transparent non-lens material, i.e. a non-light bending material, and the annular shape outer lens 290 and/or the inner round lens 292 may be positioned for example above the transparent non-lens bottom walls and secured to surrounding structure of the housing cover 40.

FIG. 2 shows an axial arrangement of the light emitting elements 24, the collimators 200, the annular shape lens 30, and the housing lens 46, where axial refers to the direction of emission of light from the light heads 12, or downward in FIG. 2. The annular shape outer lens 290 and the inner round lens 292 are in the light emitting paths LP of the plurality of light emitting elements 24. The annular shape lens 30 is in the light emitting paths LP of the plurality of light emitting elements 24, positioned between the light emitting elements 24 and the annular shape outer lens 290. The collimators 200 are also arranged in the light emitting paths LP of the plurality of light emitting elements 24 in the annular shape outer portion 140 of the light head 12 positioned between the light emitting elements 24 and the annular shape lens 30, and in the inner round portion of the light head 12 positioned between the light emitting elements 24 and the inner round lens 292.

The annular shape lens 30 and the housing lens 46, and the collimators 200 if provided, can take on any form for spreading and/or bending the light emitted by the light emitting elements 24. As shown for example in FIGS. 2 and 6, the inner round lens 292 of the housing lens 46 has a top face 320 formed as a stepped surface, for example a plurality of Fresnel wedges, that bends individual portions of the light beams, and a bottom face 324 formed as a generally planar surface. As shown for example in FIGS. 2, 8, 14, and 15, the annular shape lens 30 has a top face 340 formed as a stepped surface, for example a plurality of Fresnel wedges, that bends individual portions of the light beams, and a bottom face 344 formed as a wavy or curved surface. The annular shape outer lens 290 of the housing lens 46, meanwhile, has a top face 360 formed as a wavy or curved surface and a bottom face 364 formed as a generally planar wedge-shaped surface, where a generally planar wedge-shaped surface refers to a generally planar surface that is not perpendicular to the direction of travel of the light beam emitted by the light emitting elements 24 and collimators 200, for example. Rotation of the annular shape lens 30 and its wavy surface 344 relative to the housing lens 46 and its wavy surface 360 results in beam spreading (focusing) of the light beam, while simultaneously bending (aiming) of the light beam is achieved by the wedge-shaped surfaces 340, 364 of the annular shape lens 30 and the housing lens 46. Further details of the top and bottom face features and characteristics that may be suitable for the annular shape lens 30 ("upper lens") and the housing lens 46 ("lower lens") can be found in U.S. patent application Ser. No. 16/278,301, published as US20190258068A1, and titled "Refractive Lens Array Assembly," which is incorporated by reference for all purposes as if fully set forth herein. It will be appreciated that the annular shape lens 30 and the housing lens 46 need not be limited to the features and characteristics as shown and described herein and can include additional and/or alternate types of features and characteristics as necessary or desired to satisfy illumination requirements specific to an application. Further, it will be appreciated that the light head 12 may include additional lenses for bending and/or spreading of the light emitted by the light emitting elements 24.

Figure 8:
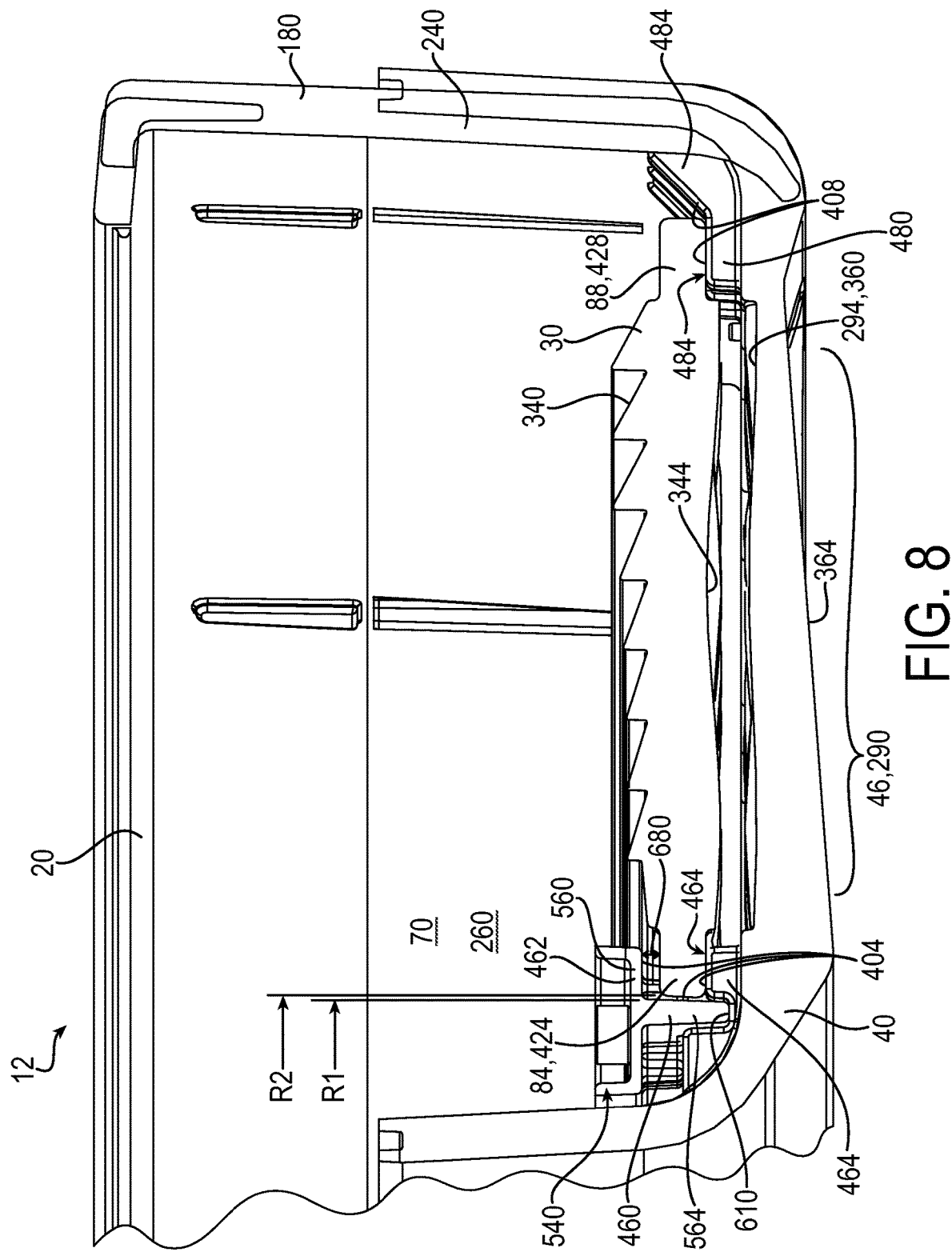
FIG. 8 is a side cross section view of a portion of the light head, showing the annular shape lens, inner periphery lower walls and outer periphery lower walls, and a lens restricting member.

Reference is now made to FIGS. 2, 6, 8, and 11-12, which show details of the annular shape lens 30 and the motion transfer member 50, and the movable interconnection between the two within the cavity 70 of the housing cover 40. The annular shape lens 30 has a boss 62 and a plurality of guide members 84, 88 at its inner periphery 384 and outer periphery 388. The motion transfer member 50 movably interacts with the boss 62 of the annular shape lens 30 to rotate the annular shape lens 30 about the rotation axis A-A and within the annular shape outer cavity 260. The guide members 84, 88 position the boss 62 of the annular shape lens 30 to movably interact with the motion transfer member 50. As shown in FIG. 8, the housing cover 40 includes within the annular shape outer cavity 260 thereof corresponding inner periphery bearing surfaces 404 and outer periphery bearing surfaces 408. To aid in the movable interaction between the annular shape lens 30 and the motion transfer member 50, including the rotation of the annular shape lens 30 within the cavity 70 of the housing cover 40, the inner periphery guide members 84 and outer periphery guide members 88 are configured to slidably contact and/or have their motion restricted and/or guided by the respective inner periphery bearing surfaces 404 and outer periphery bearing surfaces 408 of the housing cover 40. In the illustrative embodiment, the sliding contact of the guide members 84, 88 with the respective inner periphery bearing surfaces 404 and outer periphery bearing surfaces 408 results in a concentric relationship between the annular shape lens 30 and the annular shape outer cover 240 of the housing cover 40. Thus, the respective inner periphery bearing surfaces 404 and outer periphery bearing surfaces 408 of the housing cover 40 guide the guide members 84, 88 to guide the annular shape lens 30 in a concentric relationship with the annular shape outer cover 240 of the housing cover 40.

Figure 11:
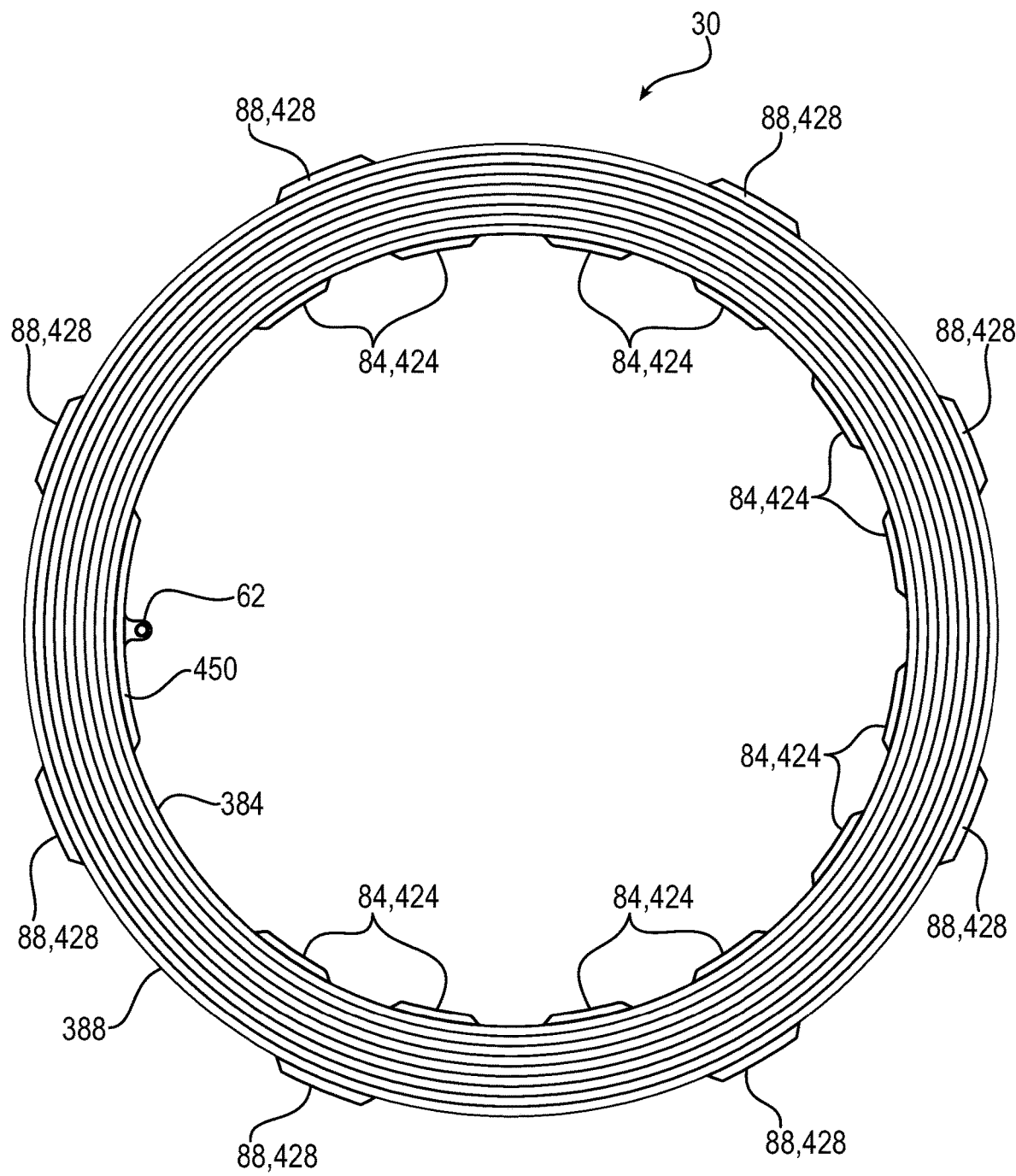
FIG. 11 is a top plan view of an annular shape lens.
Figure 12:
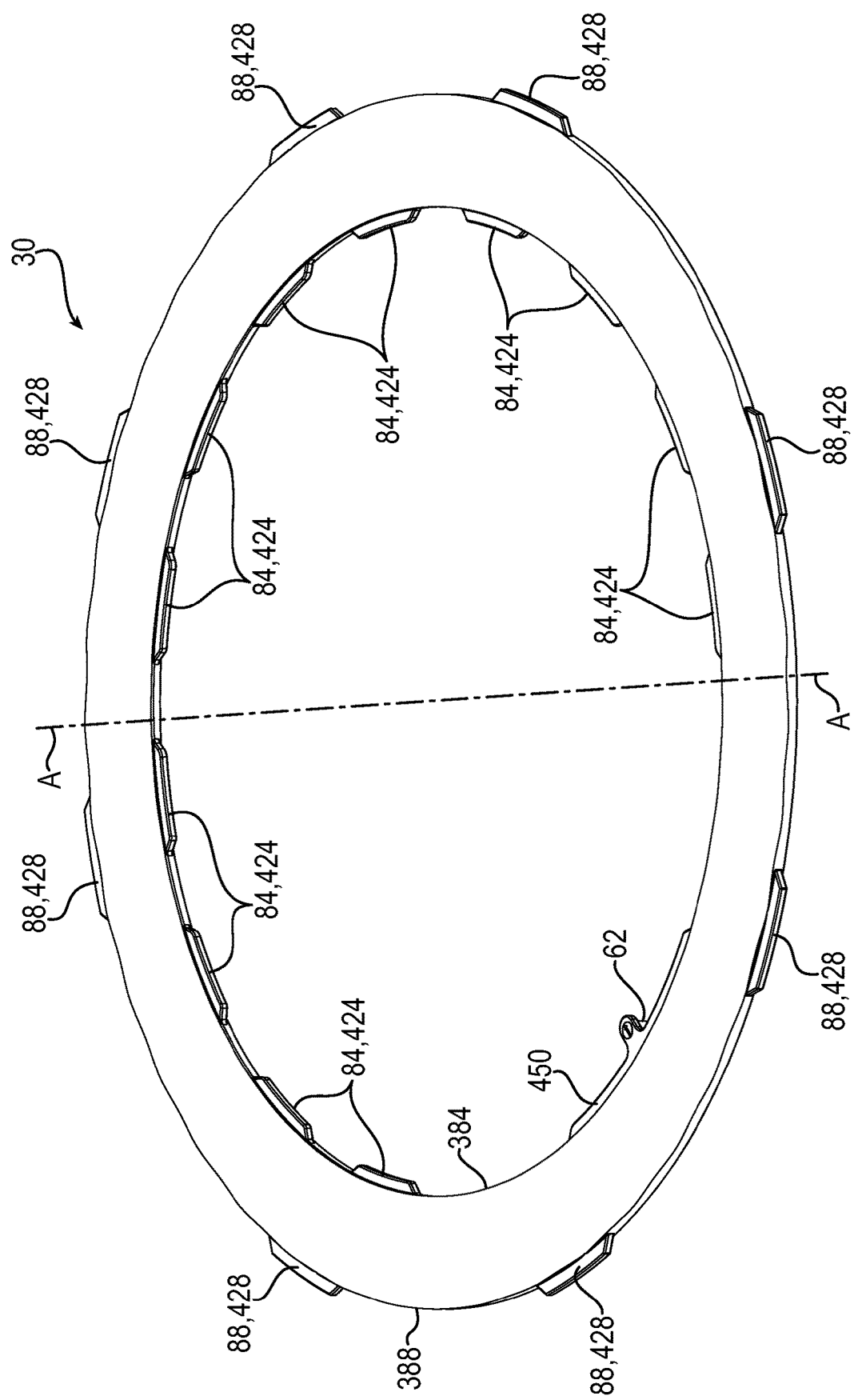
FIG. 12 is a bottom perspective view of an annular shape lens.

FIGS. 8, 11-12, and 14-15, show details of the guide members 84, 88 of the annular shape lens 30 and the bearing surfaces 404, 408 of the housing cover 40, more specifically the annular shape outer cover 240 of the housing cover 40. The inner periphery guide members 84 of the annular shape lens 30 include a plurality of radially inward tabs 424 that protrude from the inner periphery 384 of the annular shape lens 30. The outer periphery guide members 88 of the annular shape lens 30 include a plurality of radially outward tabs 428 that protrude from the outer periphery 388 of the annular shape lens 30. As shown in FIG. 11, there are 12 radially inward tabs 424 evenly spaced about 22.5 degrees apart, each having a 12 degree arcuate span, totaling an arcuate span of about 260 degrees (in the right portion of FIG. 11). In the remaining 100 degree arcuate span (in the left portion of FIG. 11), there is provided another radially inward tab 450 that protrudes from the inner periphery of the annular shape lens 30. The radially inward tab 450 has about a 35 degree arcuate span with two arcuate spaces on angularly opposite side thereof of about 32.5 degrees each. The boss 62 of the annular shape lens 30 is connected to or formed integral with the radially inward tab 450 approximately at the center of the arcuate span of the radially inward tab 450. There are eight radially outward tabs 428 evenly spaced about 45 degrees apart, each having about a 12 degree arcuate span and being separated by a circumferentially adjacent radially outward tab 428 by about a 33 degree arcuate span.

FIG. 8 shows one example of how the inner periphery bearing surfaces 404 and the outer periphery bearing surfaces 408 of the annular shape outer cover 240 may be formed. In FIG. 8, the inner periphery bearing surfaces 404 of the annular shape outer cover 240 are formed by a plurality of inner periphery upright walls 460, inner periphery upper walls 462, and inner periphery lower walls 464. The outer periphery bearing surfaces 408 of the annular shape outer cover 240 are formed by a plurality of outer periphery upright walls 480, and outer periphery lower walls 484.

Figure 16:
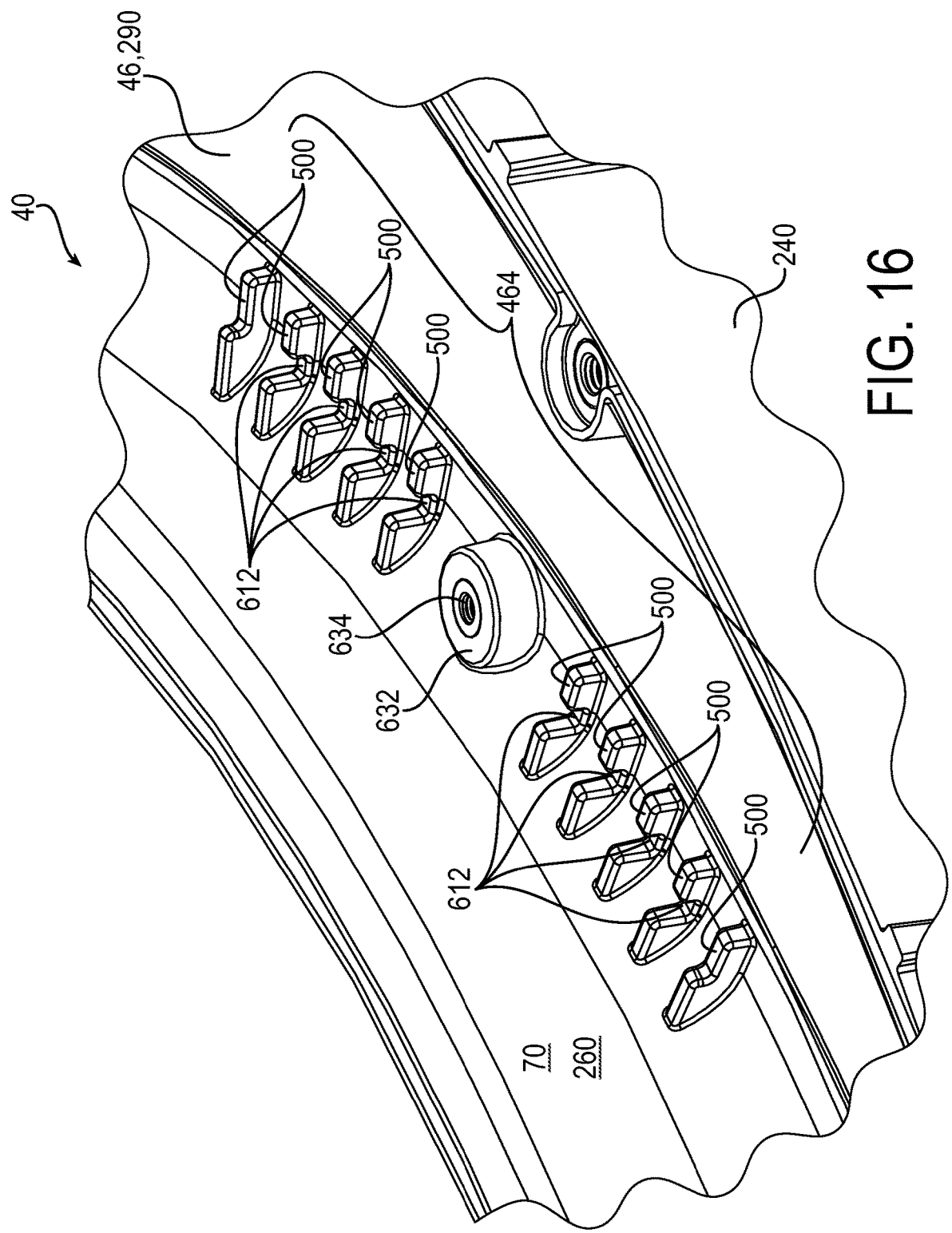
FIG. 16 is a top perspective view of a portion of the housing cover, showing inner periphery lower walls, and a surface of the housing cover for connection of a lens restricting member.

The inner periphery lower walls 464, the outer periphery upright walls 480, and the outer periphery lower walls 484 are shown in greater detail for example in FIGS. 6, 13, and 16. In the illustrative embodiment, the inner periphery lower walls 464 each comprise a set of evenly spaced ribs 500 arranged in an arc shape; the outer periphery upright walls 480 each comprise a set of evenly spaced ribs 506 arranged in an arc shape; and the outer periphery lower walls 484 each comprise a set of evenly spaced ribs 510 arranged in an arc shape. It will be appreciated that other forms are possible for example walls having other shapes or configurations. In one form, the inner periphery lower walls 464 and the outer periphery lower walls 484 may have arc shape continuous (non-ribbed) flat walls. In another form, the outer periphery upright walls 480 may project upright at right angles rather than at about 45 degrees. Referring to FIG. 13, there are 12 inner periphery lower walls 464 (in the right portion of FIG. 13) corresponding in arrangement to the respective 12 radially inward tabs 424 of the annular shape lens 30 (FIG. 11). The remaining 100 degree arcuate span (in the left portion of FIG. 13) includes the arm cover 244 and its radial arm cavity 264, which corresponds in arrangement to the radially inward tab 450 and boss 62 of the annular shape lens 30. There are eight outer periphery upright walls 480 and eight outer periphery lower walls 484 corresponding in arrangement to the respective eight radially outward tabs 428 of the annular shape lens 30.

In the illustrative embodiment, the annular shape outer cover 240 includes lens restricting members 540 that define the inner periphery upright walls 460 and inner periphery upper walls 462. As shown in FIGS. 8, 14-15, and 18-23, the lens restricting members 540 are arranged in a circumferential manner and situated within the annular shape outer cavity 260 of the annular shape outer cover 240. There are 6 lens restricting members 540, each one corresponding to two adjacent radially inward tabs 424 of the annular shape lens 30 and corresponding in arrangement to respective six sets of two adjacent radially inward tabs 424 (totaling 12 radially inward tabs 424) of the annular shape lens 30 (FIG. 11).

Figure 14:
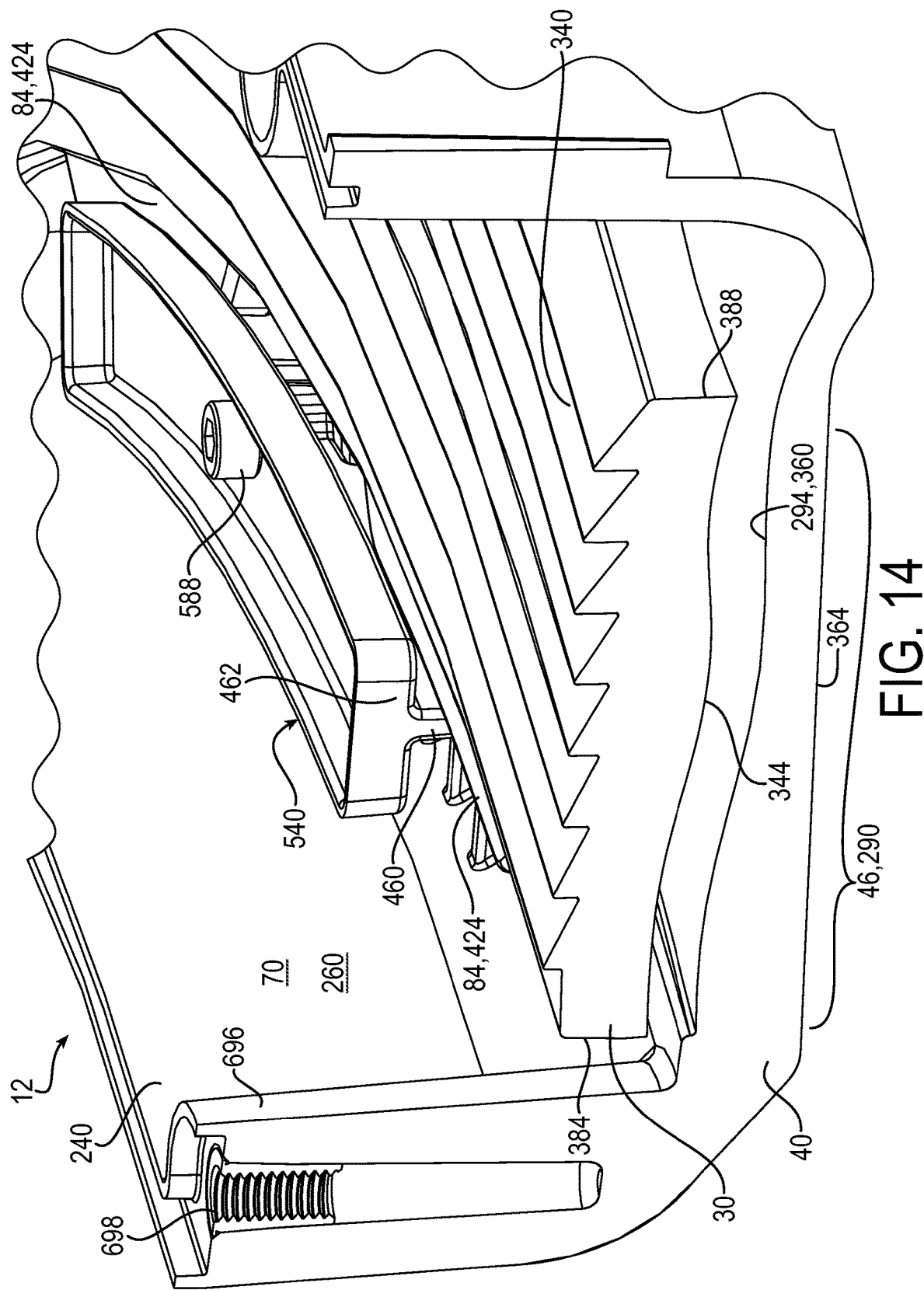
FIG. 14 is a top perspective cross section view of a lens restricting member and a portion of the housing cover and annular shape lens.
Figure 15:
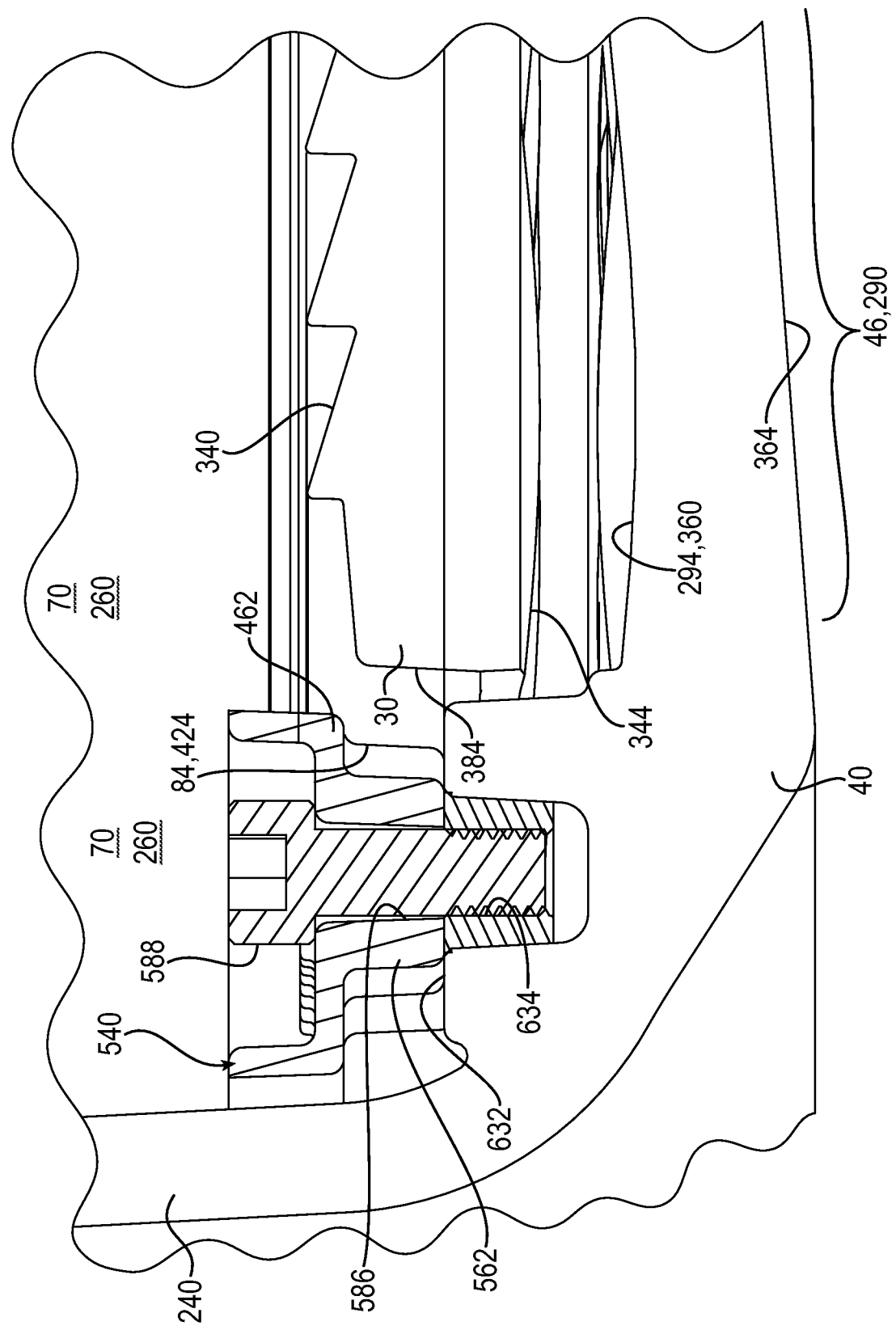
FIG. 15 is a side cross section view of a portion of the light head, showing the annular shape lens, inner periphery lower walls, and a lens restricting member fastened to a surface of the housing cover.
Figure 17:
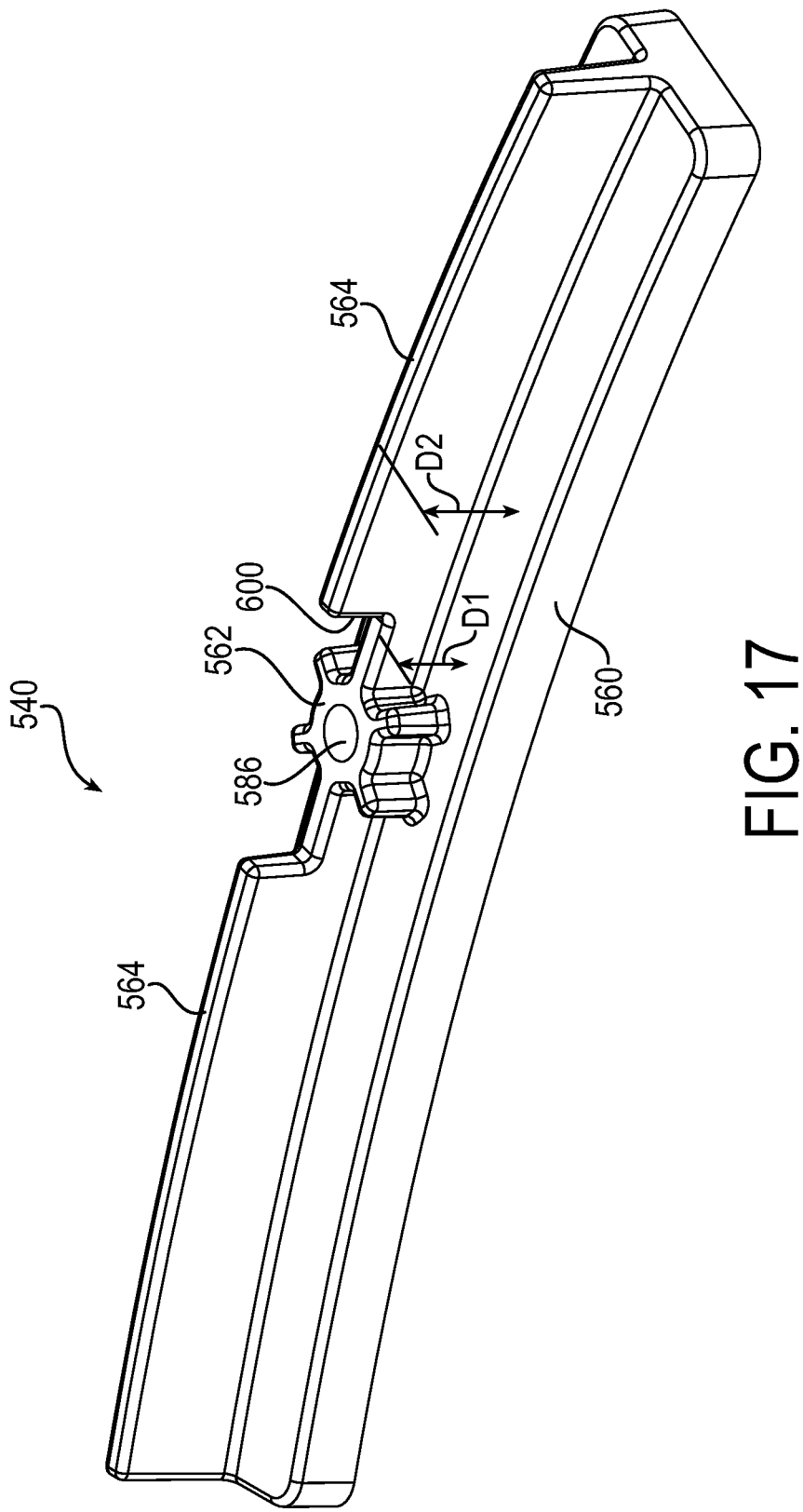
FIG. 17 is a bottom perspective view of a lens restricting member in accordance with an embodiment of the invention.

FIG. 17 shows a bottom perspective view of a lens restricting member 540. The lens restricting member 540 has an overall arc shape and includes an arc shape upper flange 560, a star shape boss 562, and a pair of arc shape lower ribs 564 at opposite sides of the star shape boss 562. The star shape boss 562 depends downward from the arc shape upper flange 560 a first distance D1, and the pair of arc shape lower ribs 564 depend downward from the arc shape flange 560 at a second distance D2 that is about two times the first distance D1. The star shape boss 562 is located approximately at the arcuate middle of the arc shape upper flange 560. The star shape boss 562 has a through hole 586 to accommodate a fastener 588, as shown in FIGS. 14 and 15. The pair of arc shape lower ribs 564 are split by an arc shape gap 600 therebetween.

Referring again to FIGS. 8, 15, and 16, the arc shape lower ribs 564 of the lens restricting member 540 sit within an arc shape groove 610 in a respective inner periphery lower wall 464. In the illustrative embodiment, the arc shape groove 610 comprises a plurality of notches 612 in the ribs 500 of the inner periphery lower wall 464. Each inner periphery lower wall 464 also has a boss 632 located approximately at the arcuate middle thereof, the boss 632 having a threaded opening 634 therein. The star shape boss 562 of the lens restricting member 540 is positioned on and secured to the boss 632 of the inner periphery lower wall 464 by inserting the fastener 588 through the through hole 586 and threading the fastener 588 into the threaded opening 634.

Once the lens restricting members 540 are installed, the arc shape lower ribs 564 of the lens restricting members 540 define the inner periphery upright walls 460 of the housing cover 40, and the arc shape upper flanges 560 define the inner periphery upper walls 462 of the housing cover 40. Referring to FIG. 8, the arc shape lower ribs 564 have an outer radius R1 that is slightly less than the inner radius R2 of the radially inward tabs 424 of the annular shape lens 30. As such, the arc shape lower ribs 564, that is the inner periphery upright walls 460, define an inner "circumferential" surface, actually a discontinuous circumferential surface, against which the radially inward tabs 424 slidably contact to restrict radial movement of the annular shape lens 30 and thus guide the annular shape lens 30 rotationally about the rotation axis A-A and within the cavity 70 of the housing cover 40. In the illustrative embodiment, the sliding contact of the radially inward tabs 424 with the respective inner upright walls 460 defined by the lens restricting members 540 results in a concentric relationship between the annular shape lens 30 and the circumferentially arranged lens restricting members 540 of the annular shape outer cover 240. Thus, the inner upright walls 460 of the lens restricting members 540 guide the radially inward tabs 424 of the annular shape lens 30 to guide the annular shape lens 30 in a concentric relationship with the circumferentially arranged lens restricting members 540 and thus the annular shape outer cover 240 of the housing cover 40.

The arc shape upper flanges 560 restrict axial movement of the radially inward tabs 424 of the annular shape lens 30. As shown in FIG. 8, once the lens restricting members 540 are installed, the arc shape upper flanges 560 lie axially above the radially inward tabs 424 of the annular shape lens 30. As such, the arc shape upper flanges 560, that is the inner periphery upper walls 462, define an upper "circumferential" surface, actually a discontinuous circumferential surface, against which the radially inward tabs 424 slidably contact to restrict upward axial movement of the annular shape lens 30 and thus guide the annular shape lens 30 rotationally about the rotation axis A-A and within the cavity 70 of the housing cover 40.

As shown in FIG. 8, the inner periphery upper walls 462 are shown positioned a predetermined clearance 680 above the radially inward tabs 424. The height of the clearance 680 is such that the radially inward tabs 424 ordinarily do not contact the inner periphery upper walls 462 when the light head's 12 light emitting paths LP are aimed at a surgical site; that is, when the light head 12 itself is positioned parallel to the surgical site as shown in FIG. 2 or tilted relative to parallel for example between 0 and 45 degrees. The clearance 680 aids in rotation of the annular shape lens 30 during ordinary usage of the light head 12 by not restricting the upper portions of the radially inward tabs 424. In the event the light head 12 is tilted such that its light is no longer emitted toward the surgical site, for example to a position 90 degrees from parallel (see FIG. 1) or even slightly upside down, for example to move the light head 12 out of the surgical area after a procedure, then the inner periphery upper walls 462 will allow the radially inward tabs 424 of the annular shape lens 30 to move axially away ("upward") from the inner periphery lower walls 464 the clearance 680 amount and thereafter restrict further axial movement. In this way, the inner periphery upper walls 462 aid in maintaining the annular shape lens 30 within the cavity 70. When the light head 12 is returned to a position at which its light is emitted toward the surgical site, the radially inward tabs 424 will move axially toward and into slidable contact with the inner periphery lower walls 464.

It will be appreciated, then, that the lens restricting members 540 together with the inner periphery lower walls 464 form a circumferential channel or groove, actually a discontinuous circumferential channel, within which the radially inward tabs 424 of the annular shape lens 30 are captured and slidably guided, aiding rotation of the annular shape lens 30 about the rotation axis A-A and within the cavity 70 of the housing cover 40. Advantageously, the circumferential channel has a low height and low width profile, which translates into a lower height light head 12 that yields improved control and handling of the light head 12 and improved laminar flow within the operating room relative to the light head 12.

Accordingly, the radially inward tabs 424 and the radially outward tabs 428 are in slidable contact with the respective inner periphery upright walls 460 and outer periphery upright walls 480. The inner periphery upright walls 460 and the outer periphery upright walls 480 restrict radial movement of the respective radially inward tabs 424 and radially outward tabs 428 and thus radial movement of the annular shape lens 30, aiding rotation of the annular shape lens 30 about the rotation axis A-A and within the cavity 70 of the housing cover 40. The radially inward tabs 424 are in slidable contact with the inner periphery lower walls 464 and the inner periphery upper walls 462. The radially outward tabs 428 are in slidable contact with the outer periphery lower walls 484. The inner periphery lower walls 464 and the inner periphery upper walls 462 restrict axial movement of the annular shape lens 30, upward and downward movement in FIG. 8, aiding rotation of the annular shape lens 30 about the rotation axis A-A and within the cavity 70 of the housing cover 40. The outer periphery lower walls 484 restrict axial movement of the radially outward tabs 428 and thus axial movement of the annular shape lens 30, downward movement in FIG. 8, aiding rotation of the annular shape lens 30 about the rotation axis A-A and within the cavity 70 of the housing cover 40.

In the illustrative embodiment, radial restriction of the annular shape lens 30 is provided by both the inner periphery guide members 84 slidably contacting the inner periphery upright walls 460 and the outer periphery guide members 88 slidably contacting the outer periphery upright walls 480. The invention need not be limited as such and other embodiments are contemplated. Thus, in one form, the annular shape lens 30 may have only inner periphery guide members 84 that slidably contact inner periphery upright walls 460 of the housing cover 40, where outer periphery guide members 88 and outer periphery upright walls 480 are omitted. In such case, the inner periphery upright walls 460, for example at diametrically opposite sides of the annular shape lens 30, restrict radial movement of the inner periphery guide members 84 and thus of the annular shape lens 30, aiding rotation of the annular shape lens 30 about the rotation axis A-A and within the cavity 70 of the housing cover 40. In an alternate form, the annular shape lens 30 may have only outer periphery guide members 88 that slidably contact outer periphery upright walls 480 of the housing cover 40, where inner periphery guide members 84 and inner periphery upright walls 460 are omitted. In such case, the outer periphery upright walls 480, for example at diametrically opposite sides of the annular shape lens 30, restrict radial movement of the outer periphery guide members 88 and thus of the annular shape lens 30, aiding rotation of the annular shape lens 30 about the rotation axis A-A and within the cavity 70 of the housing cover 40.

It will also be appreciated that the lens restricting members 540 may be provided at the outer periphery of the housing cover 40 rather than the inner periphery of the housing cover 40, in which case the corresponding outer periphery lower walls 484 would incorporate a groove and boss analogous to the groove 610 and boss 632 of the afore described inner periphery lower walls 464 to accommodate the pair of arc shape lower ribs 564 of the lens restricting members 540. Alternately, the lens restricting members 540 may be provided at both the inner periphery lower walls 464 and the outer periphery lower walls 484 of the housing cover 40.

In the illustrative embodiment, the annular shape lens 30 and housing cover 40 are arranged so that the annular shape lens 30 is slidably movable on the plurality of inner periphery lower walls 464 and the plurality of outer periphery lower walls 484. In an alternate form, the housing cover 40 may have only a plurality of inner periphery lower walls 464, and the outer periphery lower walls 484 may be omitted; and in such form, the annular shape lens 30 is slidably movable on only the inner periphery lower walls 464. In another form, the housing cover 40 may have only a plurality of outer periphery lower walls 484, and the plurality of inner periphery lower walls 464 may be omitted; and in such form, the annular shape lens 30 is slidably movable on only the outer periphery lower walls 484.

The housing base 20 may be made of metal, thermoplastic, or thermoset materials, or combinations of these materials. The annular shape outer base 180, the inner round base 182, and the radial arm base 184 may be made of the same or different materials.

The annular shape lens 30 may be made as a single integral molded component made of acrylic or other suitable transparent thermoplastic materials such as polycarbonate. Thus, the annular lens, the radially inward tabs 424, the radially outward tabs 428, the radially inward tab 450 and the boss 62, together form a single integral molded component. The inventors have found that the single integral molded component structure can contribute to the lower overall height form of the light head 12 disclosed herein. By way of example, the radially inward tab 450 and the boss 62, including their size and relative position, may be integrally molded as part of the annular shape lens 30 rather than provided as separate components requiring fasteners, threaded inserts, positioning spacers, or other connection means that typically require additional height, width, and/or weight in the overall light head 12 structure. It will be appreciated, of course, that the annular shape lens 30 may be made of metal or thermoset materials in addition to, or alternate to, thermoplastic materials, or made of combinations of these materials. In another form, the annular shape lens 30 may be made as a single integral monolithic structure by other techniques such as additive manufacturing. Further, the radially inward tabs 424, the radially outward tabs 428, the radially inward tab 450 and its boss 62, may be made of materials different than that of the annular lens. Still further, the radially inward tabs 424, the radially outward tabs 428, the radially inward tab 450 and its boss 62, may be made of the same or different materials, and/or may be made as separate components that are in turn connected to the annular lens. It will further be appreciated that the annular shape lens 30 may be made up of several arc shape pieces that when connected form an annular shape.

The housing cover 40 may be made as a single integral molded component made of transparent polycarbonate or other suitable transparent thermoplastic materials such as acrylic. Thus, the housing lens 46, the upright housing walls, the inner periphery lower walls 464, and the outer periphery lower walls 484, together form a single integral molded component. The inventors have found that the single integral molded component structure can contribute to the lower overall height form of the light head 12 disclosed herein. By way of example, the inner periphery lower walls 464 and outer periphery lower walls 484, including their size and relative position, may be integrally molded as part of the housing cover 40 rather than provided as separate components requiring fasteners, threaded inserts, positioning spacers, or other connection means that typically require additional height, width, and/or weight in the overall light head 12 structure. It will be appreciated, of course, that the housing cover 40 may be made of metal or thermoset materials in addition to, or alternate to, thermoplastic materials, or made of combinations of these materials. In another form, the housing cover 40 may be made as a single integral monolithic structure by other techniques such as additive manufacturing. Further, the upright housing walls, the inner periphery lower walls 464, and the outer periphery lower walls 484, may be made of materials different than that of the housing lens 46. Still further, the upright housing walls, the inner periphery lower walls 464, and the outer periphery lower walls 484, may be made of the same or different materials, and/or may be made as separate components that are in turn connected to the housing lens 46. In addition, the annular shape outer portion 140, the inner round portion, and the radial arm may be made of the same or different materials, and/or may be made as separate components that are in turn connected.

The housing base 20 and the housing cover 40 are connected by fasteners 686. In the illustrative embodiment, the fasteners 686 pass through through holes 692 in the housing base 20 and thread into corresponding threaded openings 696 in bosses 698 of the housing cover 40. The bosses 698 are circumferentially arranged and circumferentially spaced for example as shown in FIGS. 18 and 20-23. As is also shown in FIGS. 18 and 20-23, the radially inward tabs 424 of the annular shape lens 30 protrude into the respective spaces between circumferentially adjacent bosses 698. Likewise, the circumferentially arranged lens restricting members 540 and the bosses 632 to which the lens restricting members 540 connects, reside in the respective spaces between circumferentially adjacent bosses 698. A seal may be provided in and/or around the connection seam of the housing base 20 and housing cover 40 for dust and fluid ingress protection.

In the illustrative embodiment, the annular shape lens 30 is circular and the rotation axis A-A constitutes the central axis of the circular annular shape lens 30. It will be appreciated that the annular shape lens 30 may have any curvilinear shape, whether circular as shown, elliptical, oval, among others. Moreover, the rotation axis A-A may be other than a central axis of the circular annular shape lens 30. For example, the rotation axis A-A may be offset from the central axis of the circular annular shape lens 30.

Also, in the illustrative embodiment, the rotation axis A-A constitutes the central axis of the light head 12 including the central axis of the housing base 20 and the central axis of the housing cover 40. The rotation axis A-A of the annular shape lens 30 need not be the same as (coincide with) the central axis of the light head 12 itself, or the same as (coincide with) the central axis of the housing base 20 and/or the housing cover 40. Thus, for example, the rotation axis A-A of the annular shape lens 30 may be offset from the central axis of the housing base 20 and/or housing cover 40, particularly where the light head 12 includes additional or alternate type control elements, handles, connection brackets, contours, among others.

Turning briefly to FIGS. 18-23, the guide members 84, 88 position the boss 62 of the annular shape lens 30 to movably interact with the motion transfer member 50, where movably interact refers to the boss 62 and thus the annular shape lens 30 being movable by interaction with the motion transfer member 50. Thus, for example, the radially inward tabs 424 and the radially outward tabs 428, which slidably contact the respective inner periphery bearing surfaces 404 and outer periphery bearing surfaces 408 of the housing cover 40, position the boss 62 of the annular shape lens 30 to movably interact with the motion transfer member 50 to aid in rotation of the annular shape lens 30 about the rotation axis A-A and within the cavity 70. In the movable interaction in FIGS. 18, 20, and 22, the motion transfer member 50 moves the boss 62 and thus the annular shape lens 30 to, respectively, a neutral position, a position counterclockwise from the neutral position, and a position clockwise from the neutral position, from a perspective of looking from above the light head 12 downward into the cavity 70 of the light head 12.

Referring now to FIGS. 2-4, 7 and 10, a driving source 104 and a motion transfer member 50 for imparting motion to the boss 62 of the annular shape lens 30 will now be described.

In the illustrative embodiment, the driving source 104 includes a handle 714. It will be appreciated that that the light head 12 may incorporate alternate or additional types of driving sources. In one form, the driving source 104 may include a lever depending downward from the bottom of the light head 12 in a manner like that of the illustrative handle 714 and operatively coupled to the motion transfer member 50. In another form, the driving source 104 may be a slider that is slidable relative to a bottom surface of the light head 12 and operatively coupled to the motion transfer member 50. In still another form, the driving source 104 may include a rotary motor or linear motor operable for example by control elements in a surface the light head 12 and operatively coupled to the motion transfer member 50, or even a rotary motor or linear motor that is operable by a handle of the light head 12.

In the illustrative embodiment, the motion transfer member 50 includes a lever 740. As was briefly noted above, the motion transfer member 50 may take on other forms. For example, the motion transfer member 50 may include a gear assembly whereby the driving source 104 imparts movement to a rotary gear or rack and the rotary gear or rack, in turn, impart motion to the annular shape lens 30. It will be appreciated that the motion transfer member 50 may be a series of levers and/or gears and/or gear trains, or any other type of motion transfer mechanism and/or articulating assembly capable of conveying motion from the driving source 104 to the annular shape lens 30.

Figure 7:
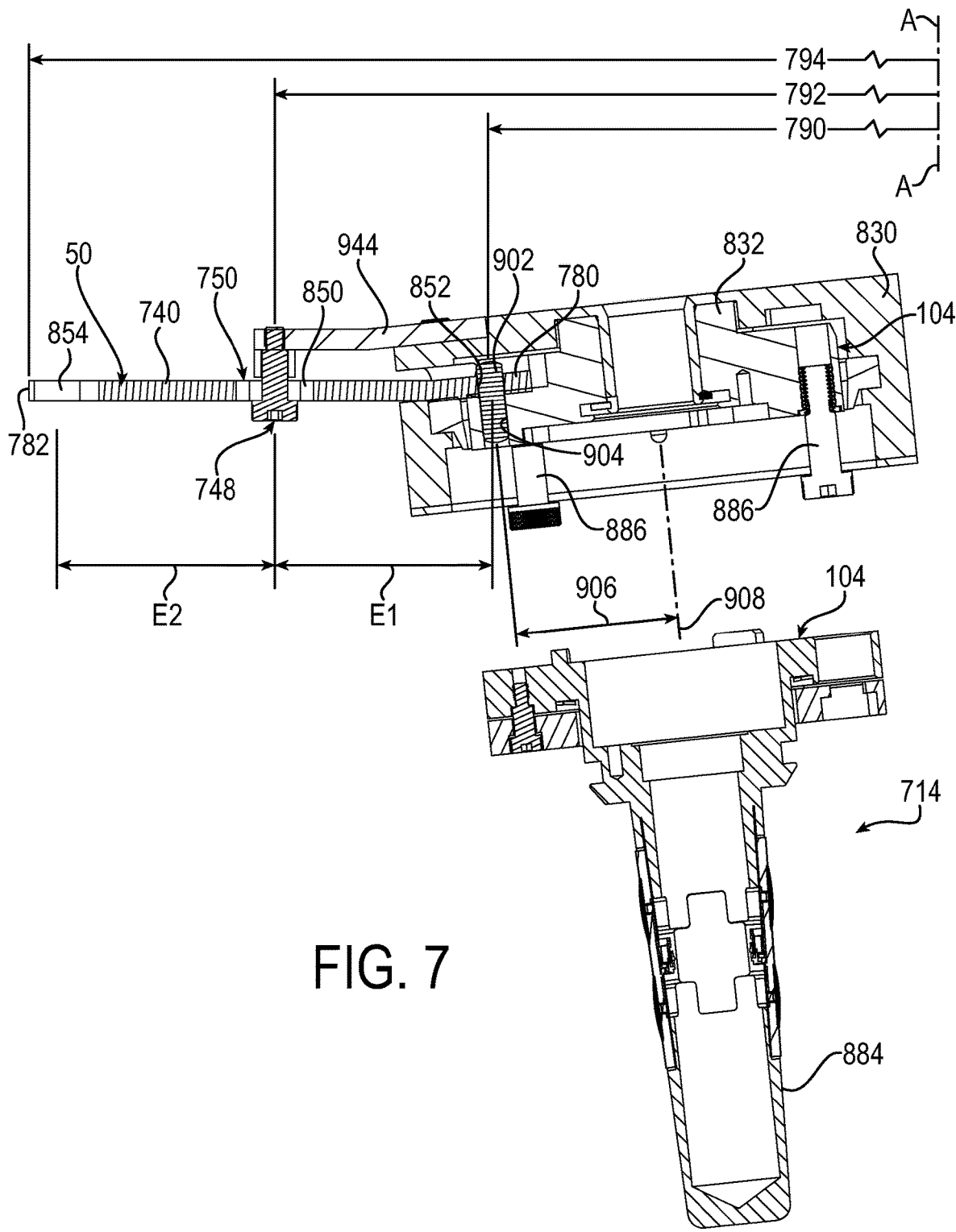
FIG. 7 is a side cross section view of a lever, hub, and a grip portion of a handle, showing the grip portion disconnected from the hub.
Figure 10:
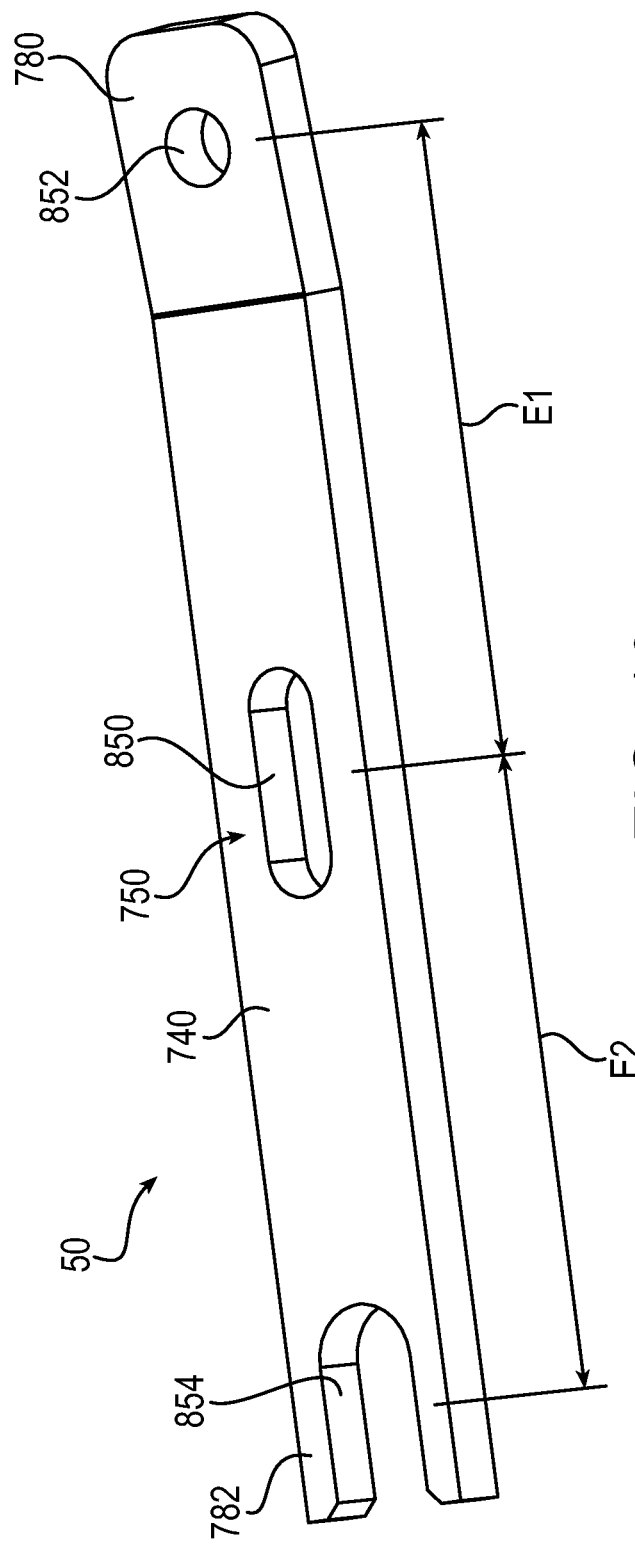
FIG. 10 is a top perspective view of a motion transfer member.

The lever 740 is movable relative to a fulcrum 748 of the light head 12 at a pivot slider portion 750 of the lever 740. As shown in FIG. 2, the entire lever 740 is configured to move relative to the fulcrum 748 within the depth of the cavity 70. Referring to FIGS. 2, 7, and 10, the lever 740 includes a first end 780 and a second end 782 at opposite sides of the pivot slider portion 750 and thus at opposite sides of the fulcrum 748. The first end 780, the fulcrum 748, and the second end 782 are arranged at respective first, second, and third radial distances 790, 792, 794 from the rotation axis A-A, wherein the third radial distance 794 is greater than the second radial distance 792, and the second radial distance 792 is greater than the first radial distance 790. The inventors have found that the afore arrangement of the lever 740 within the housing cover 40 contributes to a lower height light head 12 and facilitates a C-shape opening in the light head 12 structure that improves laminar flow in the vicinity of the light head 12.

The first end 780 is spaced a first distance E1 from the fulcrum 748. The second end 782 is spaced a second distance E2 from the fulcrum 748. The lever 740 is configured to transfer motion from the driving source 104 at the first end 780 of the lever 740 into rotational motion of the annular shape lens 30 about the rotation axis A-A and within the cavity 70 at the second end 782 of the lever 740 in response to movement of the lever 740, and more specifically the pivot slider portion 750 of the lever 740, relative to the fulcrum 748. The degree of motion from the driving source 104 and the resultant degree of rotation of the annular shape lens 30 is based on the ratio of the first distance E1 from the fulcrum 748 to the second distance E2 from the fulcrum 748. Accordingly, the location of the pivot slider portion 750 of the lever 740 provides the desired ratio of driving source 104 motion to annular shape lens 30 rotation. Thus, where the first and second distances E1, E2 are approximately equal and the driving source 104 imparts a driving motion on the first end 780 of the lever 740 about the fulcrum 748 of for example 5 degrees, the resultant degree of rotation of the annular shape lens 30 about the rotation axis A-A at the second end 782 of the lever 740 is about 5 degrees. Where the first distance E1 is greater than the second distance E2 and the driving source 104 imparts a driving motion on the first end 780 of the lever 740 about the fulcrum 748 of for example 5 degrees, the resultant degree of rotation of the annular shape lens 30 about the rotation axis A-A at the second end 782 of the lever 740 will be less than 5 degrees. Where the first distance E1 is less than the second distance E2 and the driving source 104 imparts a driving motion on the first end 780 of the lever 740 about the fulcrum 748 of for example 5 degrees, the resultant degree of rotation of the annular shape lens 30 about the rotation axis A-A at the second end 782 of the lever 740 will be greater than 5 degrees.

As shown in the embodiment of FIGS. 2 and 7, in which the driving source 104 includes the handle 714, the handle 714 is rotatably mounted coaxially to a hub 830 of the light head 12. The first end 780 of the lever 740 is movably coupled to a bushing 832 of the handle 714 and the second end 782 of the lever 740 is movably coupled to the annular shape lens 30. The lever 740 is configured to transfer rotational motion of the handle 714 at the first end 780 of the lever 740 into rotational motion of the annular shape lens 30 at the second end 782 of the lever 740. Here, the degree of rotation of the handle 714 and the resultant degree of rotation of the annular shape lens 30 is based on the ratio of the first distance E1 from the fulcrum 748 to the second distance E2 from the fulcrum 748. Accordingly, the location of the pivot slider portion 750 of the lever 740 provides the desired ratio of handle 714 rotation to annular shape lens 30 rotation.

FIG. 10 shows an example of a lever 740 suitable for transferring movement from the handle 714 to the annular shape lens 30. The lever 740 has an elongated shape. The pivot slider portion 750 of the lever 740 which is movably coupled to the fulcrum 748 of the light head 12 is located approximately at the center of the length of the lever 740 and defines therein an elongated central slot 850 that extends in the elongated direction of the lever 740. The first end 780 of the lever 740, i.e. the end of the lever 740 movably coupled to the handle 714, has a through hole 852. The second end 782 of the lever 740, i.e. the end of the lever 740 movably coupled to the annular shape lens 30, defines therein an elongated outward slot 854 that extends in the elongated direction of the lever 740 and opens outwardly in a direction away from the fulcrum 748.

FIGS. 2 and 7 show the coupling of the first end 780 of the lever 740 to the bushing 832 of the handle 714. The bushing 832 is rotatably mounted coaxially within the hub 830 which in turn is secured to the housing cover 40 for example by fasteners 870 shown in FIGS. 3, 4, and 19. As shown in FIG. 7, a grip portion 884 of the handle 714 is removably connectable to the bushing 832 by for example fasteners 886 shown in FIGS. 2-4 and 19. Once the grip portion 884 is connected to the bushing 832, the two rotate together as a single component, i.e. the handle 714 referred to herein. The grip portion 884 typically is covered by a handle cover 890 for example as shown in FIG. 1. It will be appreciated that other grip and bushing configurations and other connection means are possible. As shown in FIGS. 2 and 7, the first end 780 of the lever 740 is movably coupled to the bushing 832 of the handle 714 by a pin 902 secured in an opening 904 of the bushing 832 a radial distance 906 from, and parallel to, a central axis 908 of the hub 830. The pin 902 is rotatably mounted in the through hole 852 of the first end 780 of the lever 740. As will be appreciated, rotation of the handle 714 rotates the pin 902 and thus the first end 780 of the lever 740 along an arc shape path 920 defined by the radial distance 906. The pin 902 rotates within the through hole 852 of the first end 780 of the lever 740 during such rotation. In an alternate form, the pin 902 may be secured in the through hole 852 of the lever 740 and rotatably mounted in the opening 904 of the bushing 832.

Figure 24:
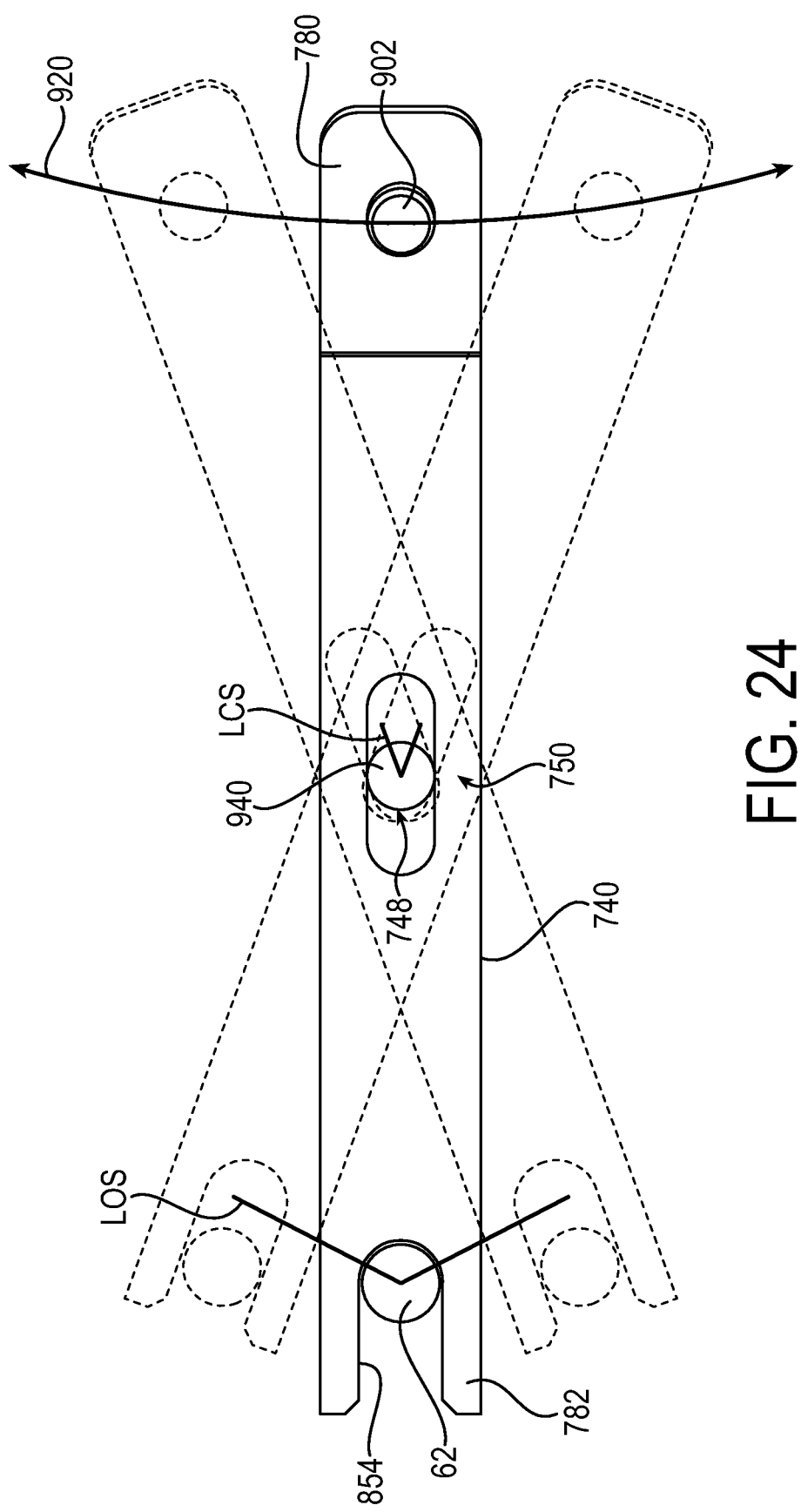
FIG. 24 shows a movement locus of a central portion of a lever and movement locus of an end of the lever.

FIGS. 2-4 and 7 show details of the fulcrum 748 coupled to a structure of the light head 12 and the lever 740 movably coupled to the fulcrum 748. In the illustrative embodiment, the fulcrum 748 includes a round shape fastener 940 connected to a bracket 944 that is in turn secured to the hub 830 of the light head 12. The illustrated round shape fastener 940 is a shoulder bolt. The diameter of the head 12 of the shoulder bolt is greater than the width of the elongated central slot 850 of the lever 740, while the diameter of the shank is slightly less than the width of the elongated central slot 850. In an alternate form, the fulcrum 748 and bracket 944 may constitute a single molded component made of for example a thermoplastic material. In an alternate form, the bracket 944 may be secured to the housing cover 40 or the housing base 20, or any combination of the hub 830, housing cover 40, and housing base 20. As shown in FIGS. 2-4 and 7, the central portion of the lever 740 is movably coupled to the shoulder bolt by the shank of the shoulder bolt being slidably movable within the elongated central slot 850 of the lever 740. As will be appreciated, owing to the first end 780 of the lever 740 moving along the arc shape path 920 about the hub central axis 908 and the fulcrum 748 being fixed relative to the hub central axis 908, the central portion of the lever 740 via the elongated central slot 850 will both pivot about and slide along the shank of the shoulder bolt when the first end 780 of the lever 740 is moved by the handle 714. An example of a movement locus LCS of the central portion of the lever 740 is shown schematically in FIG. 24.

Still referring to FIGS. 2-4 and 7, details of the coupling of the second end 782 of the lever 740 to the annular shape lens 30 will now be described. The second end 782 of the lever 740 is movably coupled to the annular shape lens 30 by the afore described boss 62 of the annular shape lens 30. In the illustrative embodiment, the boss 62 has a round shape. As shown in FIGS. 2-4 and 7, the second end 782 of the lever 740 is movably coupled to the boss 62 by the boss 62 being slidably movable within the elongated outward slot 854 of the lever 740. As will be appreciated, owing to the first end 780 of the lever 740 moving along the arc shape path 920 about the hub central axis 908 and the fulcrum 748 being fixed relative to the hub central axis 908, the second end 782 of the lever 740 via the elongated outward slot 854 will both pivot about and slide along the boss 62 when the first end 780 of the lever 740 is moved by the handle 714. An example of a movement locus LOS of the second end 782 of the lever 740 is shown schematically in FIG. 24.

Reference is now made to FIGS. 18 and 20-23, which show the various positions of the lever 740 and the annular shape lens 30 when the two movably interact relative to one another from a perspective of looking from above the light head 12 downward into the cavity 70 of the light head 12. As will be appreciated, the rotation of the handle 714 moves the first end 780 of the lever 740 relative to the fulcrum 748, which translates into movement of the boss 62 at the second, or opposite, end of the lever 740 to rotate the annular shape lens 30 about the rotation axis A-A and within the cavity 70 of the housing cover 40. As will be further appreciated, in the illustrative embodiment clockwise rotation of the handle 714 results in counterclockwise rotation of the annular shape lens 30, and counterclockwise rotation of the handle 714 results in clockwise rotation of the annular shape lens 30.

Figure 18:
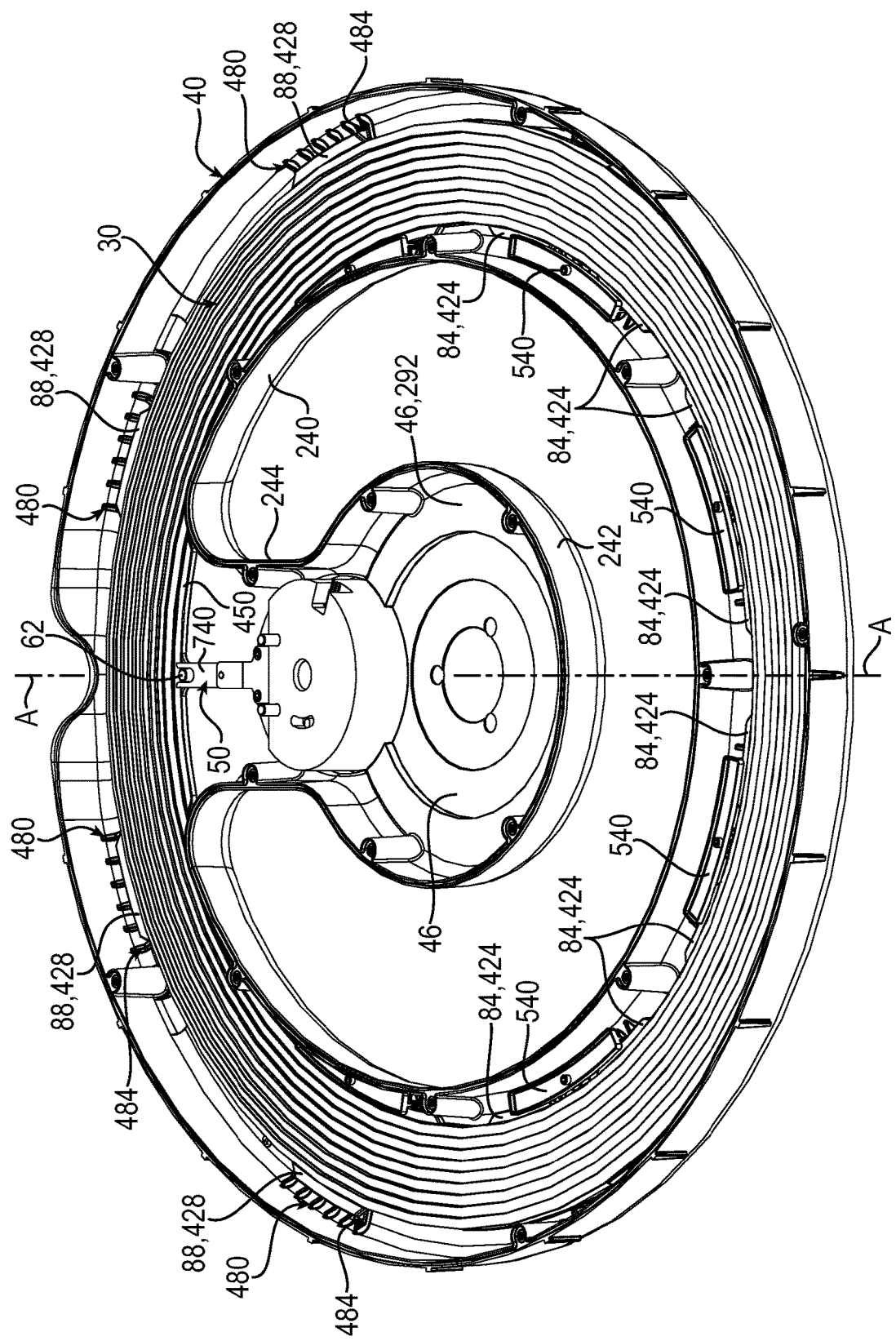
FIG. 18 is a top perspective view of the housing cover, hub, annular shape lens, and motion transfer member arranged in accordance with an embodiment of the invention, showing the annular shape lens positioned in a neutral position.
Figure 19:
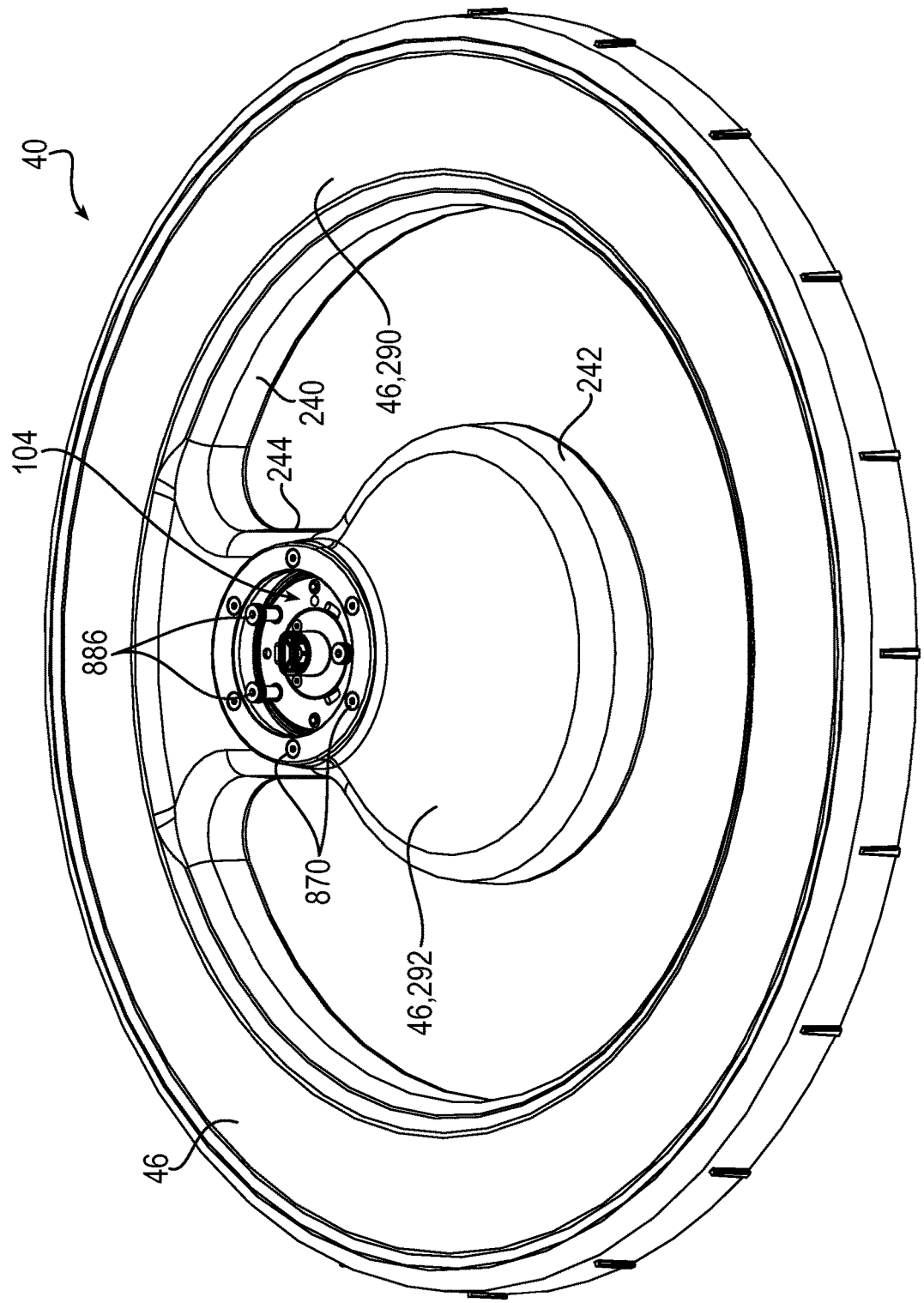
FIG. 19 is a bottom perspective view of the FIG. 18 arrangement with the annular shape lens and motion transfer member omitted for clarity.
Figure 20:
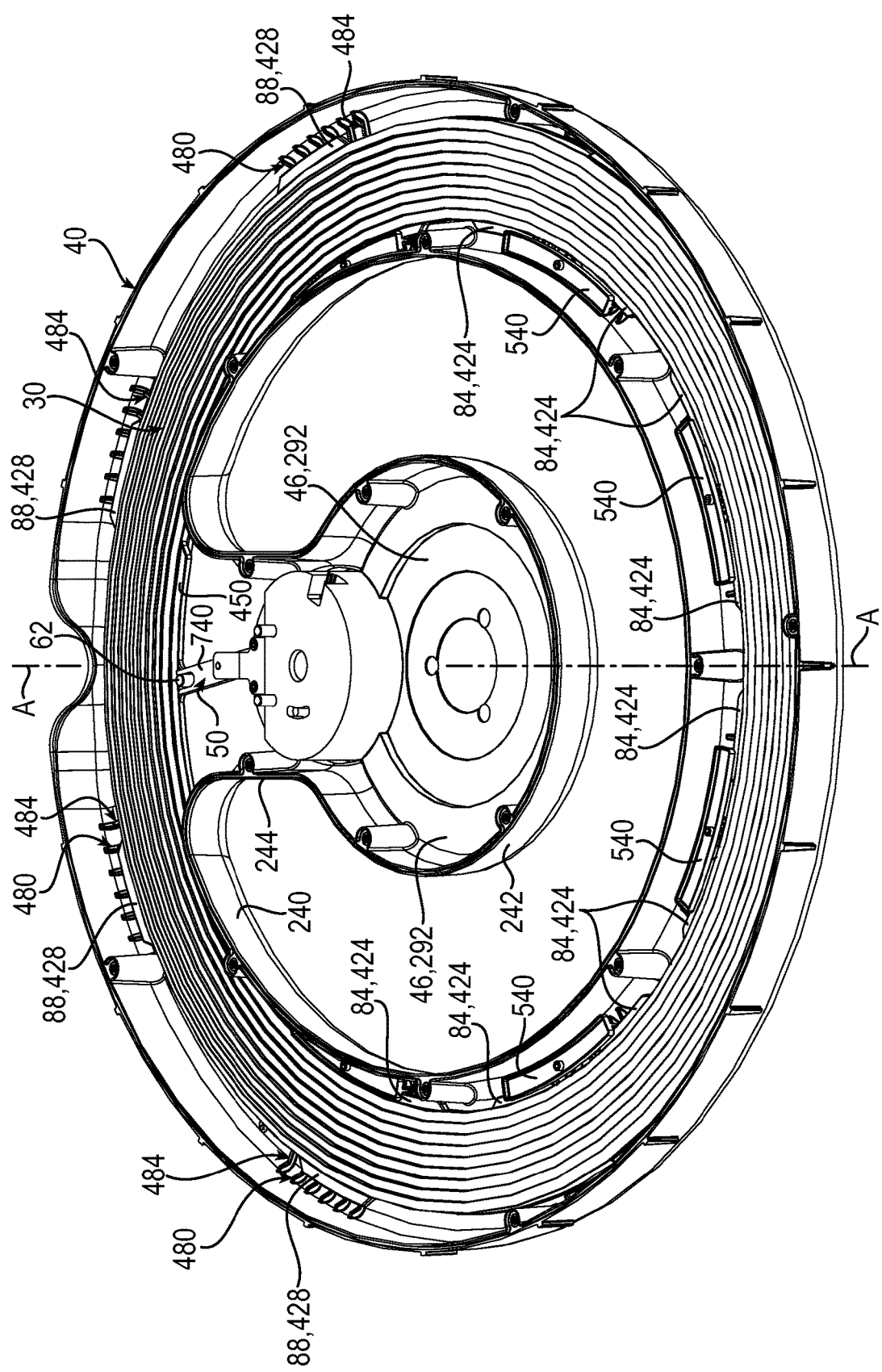
FIG. 20 is a similar view as shown in FIG. 18 except showing the annular shape lens positioned counterclockwise relative to the neutral position from a perspective of looking from above the light head downward into the cavity of the light head.
Figure 21:
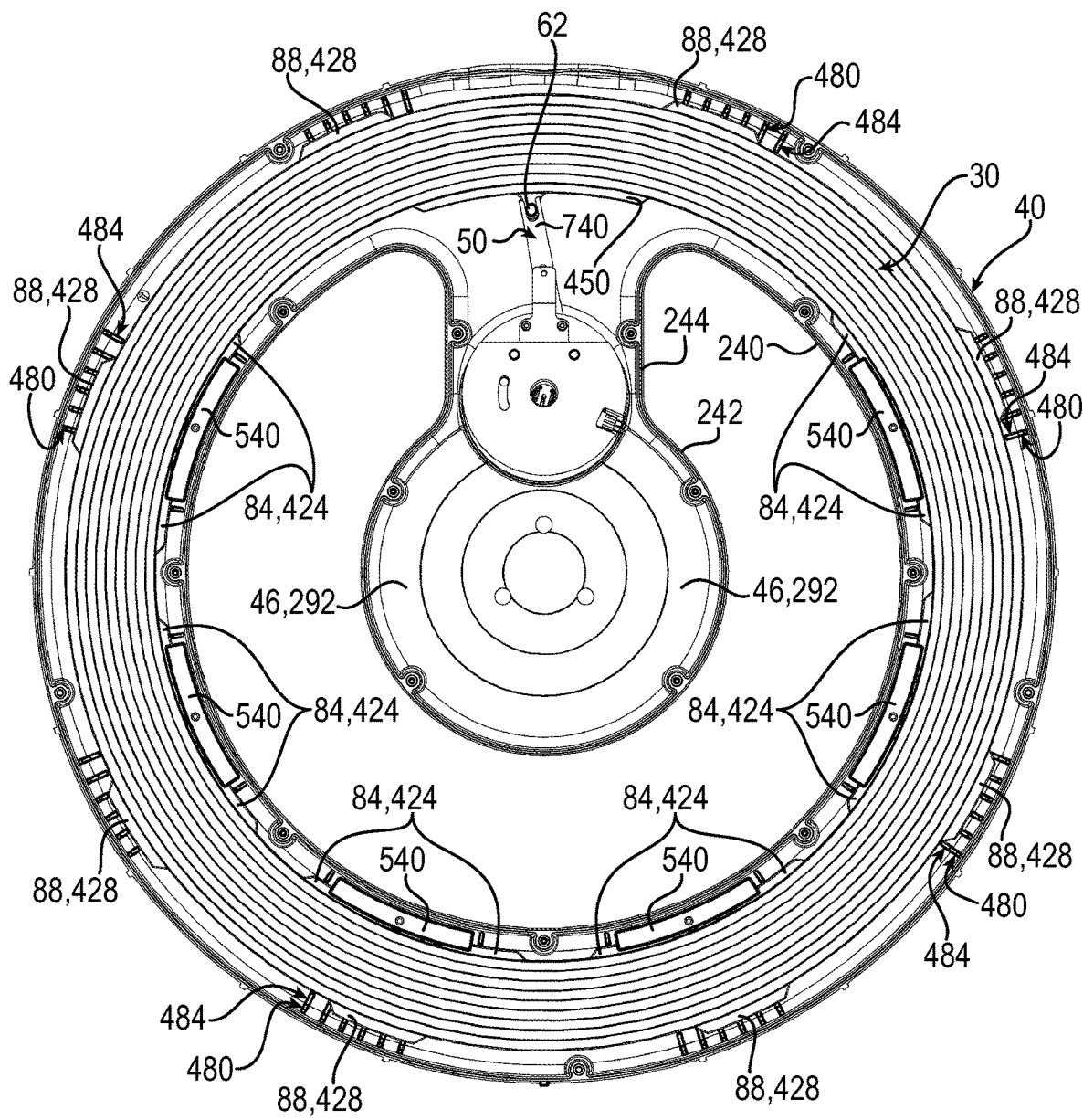
FIG. 21 is a top plan view of the FIG. 20 position of the annular shape lens.
Figure 22:
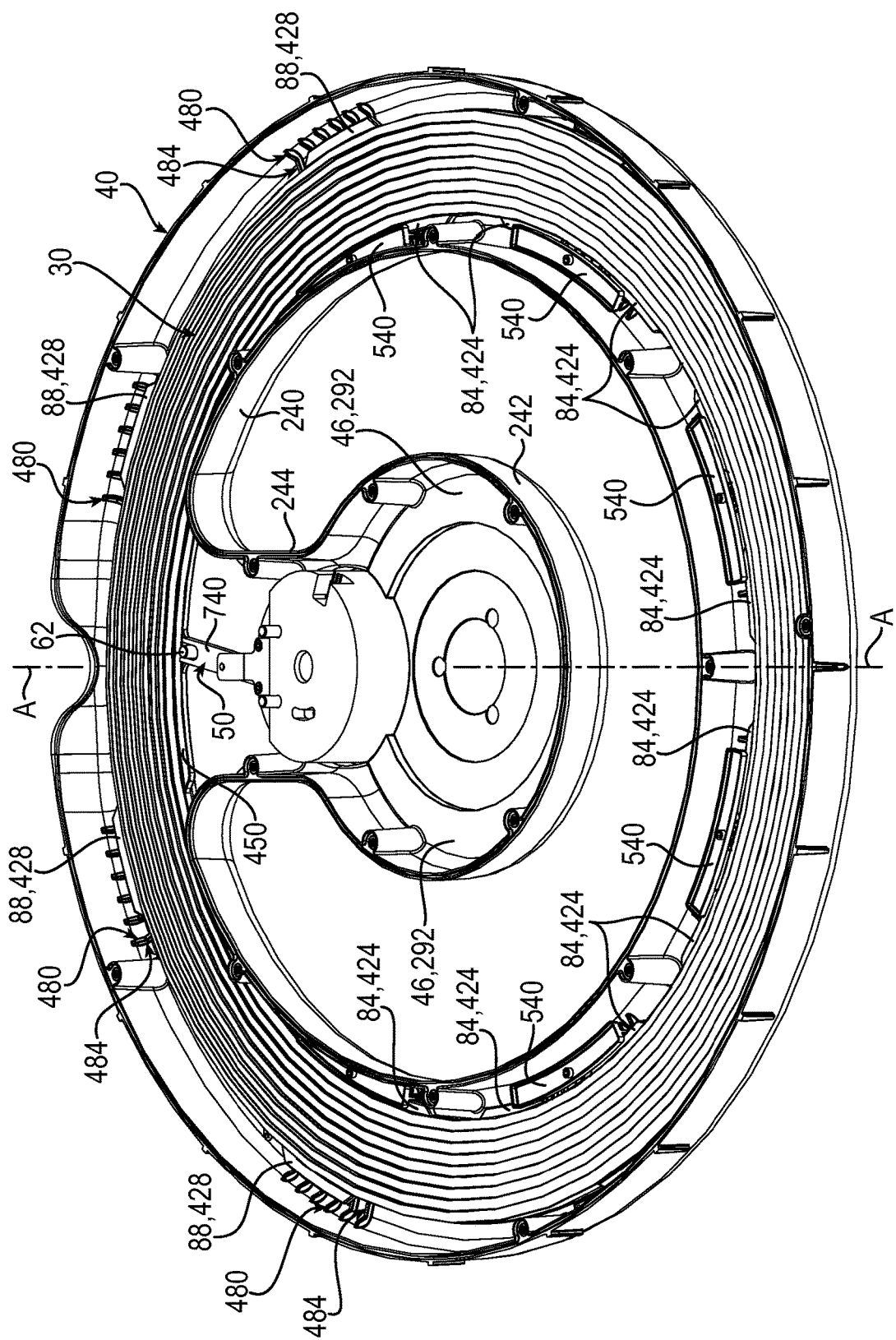
FIG. 22 is a similar view as shown in FIG. 18 except showing the annular shape lens positioned clockwise relative to the neutral position from a perspective of looking from above the light head downward into the cavity of the light head.
Figure 23:
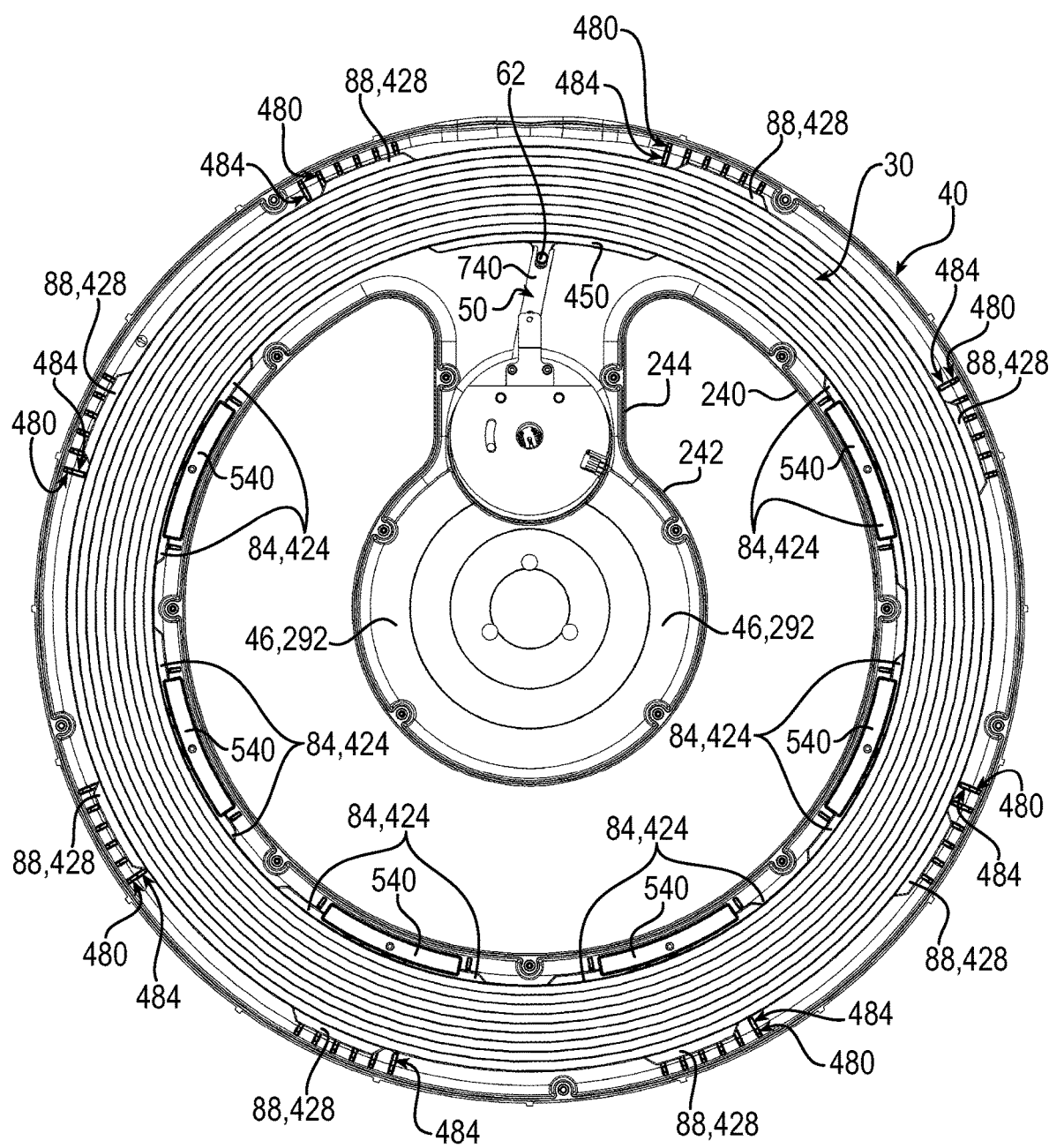
FIG. 23 is a top plan view of the FIG. 22 position of the annular shape lens.

FIG. 18 shows the annular shape lens 30 in a neutral position. In the neutral position, the lever 740 protrudes substantially radially relative to the rotation axis A-A. FIGS. 20-21 show the lever 740 rotated counterclockwise about the fulcrum 748, and the boss 62 of the annular shape lens 30 rotated counterclockwise about the rotation axis A-A. Comparing FIGS. 20-21 to FIG. 18, and referring to FIG. 24, it will be appreciated that the lever 740 is "pulled" or retracted slightly inward by the pin 902 coupled to the handle 714, causing the lever 740 to slide via the slots 850, 854 along the respective fulcrum 748 and boss 62. As will also be appreciated, the guide members 84, 88 of the annular shape lens 30 position the boss 62 to movably interact with the second end 782 of the lever 740, and the second end 782 of the lever 740 movably interacts with the boss 62 to rotate the annular shape lens 30 about the rotation axis A-A and within the cavity 70 of the housing cover 40. FIGS. 22-23 show the lever 740 rotated clockwise about the fulcrum 748, and the boss 62 of the annular shape lens 30 rotated clockwise about the rotation axis A-A. Comparing FIGS. 22-23 to FIG. 18, and referring to FIG. 24, it will be appreciated that the lever 740 is "pulled" or retracted slightly inward by the pin 902 coupled to the handle 714, causing the lever 740 to slide via the slots 850, 854 along the respective fulcrum 748 and boss 62. As will also be appreciated, the guide members 84, 88 of the annular shape lens 30 position the boss 62 to movably interact with the second end 782 of the lever 740, and the second end 782 of the lever 740 movably interacts with the boss 62 to rotate the annular shape lens 30 about the rotation axis A-A and within the cavity 70 of the housing cover 40.

Figure 25:
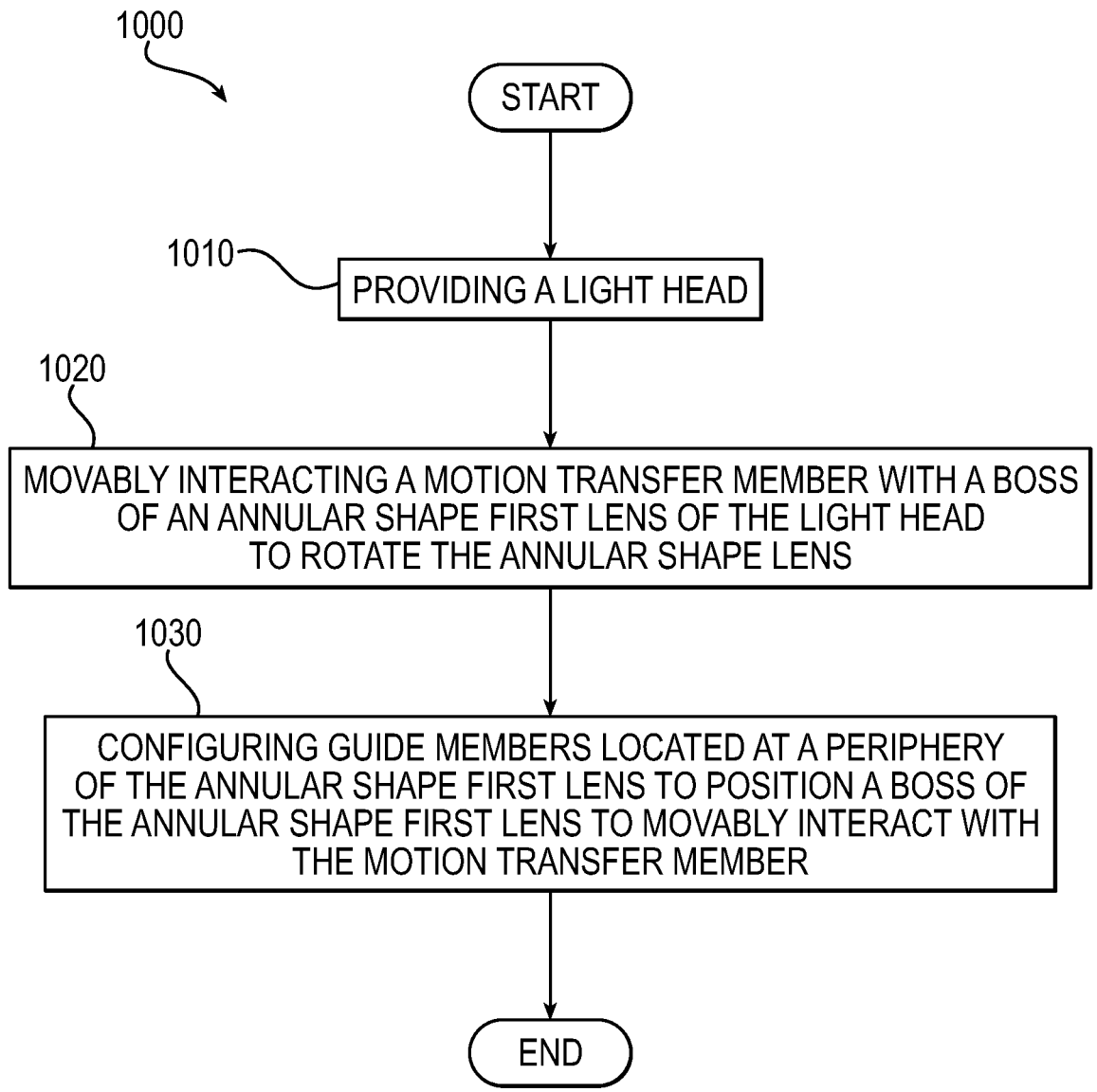
FIG. 25 shows a flowchart of a method in accordance with an embodiment of the invention.

Referring now to FIG. 25, there is shown a flowchart 1000 of a method of operating a light head of a medical device support system, such as the afore described light head 12 of the medical device support system 10 of FIG. 1, in accordance with an embodiment of the invention. At step 1010, a light head is provided that includes a housing base 20 including a plurality of light emitting elements 24; an annular shape first lens that has a rotation axis A-A; a housing cover 40 including a cavity 70 within which the annular shape first lens is rotatable about the rotation axis A-A, wherein the housing cover 40 includes a second lens; wherein the annular shape first lens and the second lens are in a light emitting path 12 of the plurality of light emitting elements 24. At step 1020, a motion transfer member 50 is movably interacted with a boss 62 of the annular shape first lens to rotate the annular shape first lens about the rotation axis A-A and within the cavity 70. At step 1030, guide members 84, 88 located at a periphery of the annular shape first lens are configured to position the boss 62 of the annular shape first lens to movably interact with the motion transfer member 50.

Figure 26:
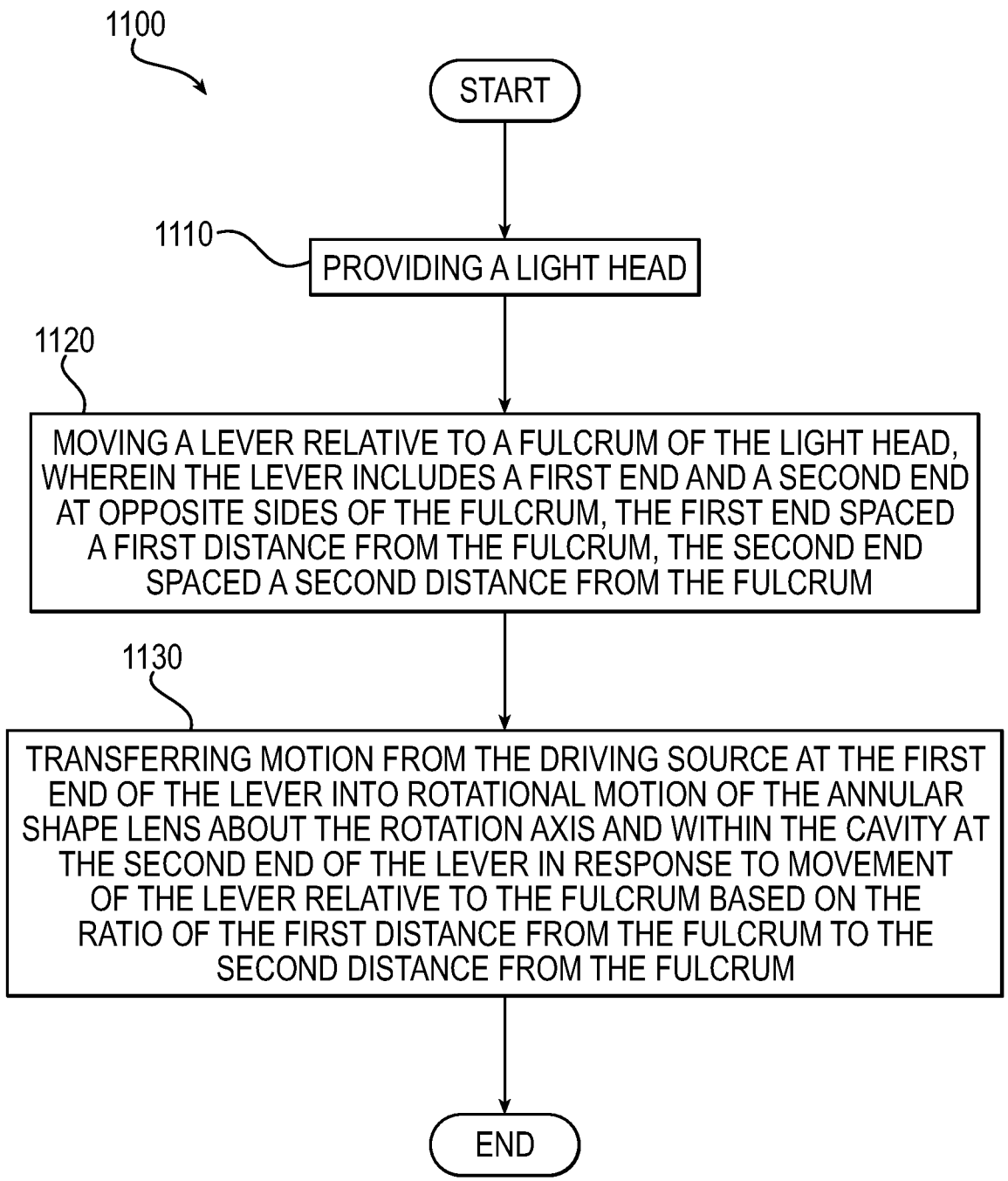
FIG. 26 shows a flowchart of a method in accordance with another embodiment of the invention.

FIG. 26 shows a flowchart 1100 of a method of operating a light head of a medical device support system, such as the afore described light head 12 of the medical device support system 10 of FIG. 1, in accordance with another embodiment of the invention. At step 1110, a light head 12 is provided that includes: a housing base 20 including a plurality of light emitting elements 24; an annular shape first lens that has a rotation axis A-A; a housing cover 40 including a cavity 70 within which the annular shape first lens is rotatable about the rotation axis A-A, wherein the housing cover 40 includes a second lens; wherein the annular shape first lens and the second lens are in a light emitting path 12 of the plurality of light emitting elements 24; and a driving source 104. At step 1120, a lever 740 is moved relative to a fulcrum 748 of the light head 12, wherein the lever 740 includes a first end 780 and a second end 782 at opposite sides of the fulcrum 748, the first end 780 spaced a first distance E1 from the fulcrum 748, the second end 782 spaced a second distance E2 from the fulcrum 748. At step 1130, motion from the driving source 104 at the first end 780 of the lever 740 is transferred into rotational motion of the annular shape first lens about the rotation axis A-A and within the cavity 70 at the second end 782 of the lever 740 in response to movement of the lever 740 relative to the fulcrum 748 based on the ratio of the first distance from the fulcrum 748 to the second distance from the fulcrum 748.

Although the invention has been shown and described with respect to a certain embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A light head for a medical device support system, comprising:
    a housing base including a plurality of light emitting elements;
    an annular shape first lens that has a ring shape and a rotation axis, the ring shape first lens having an inner periphery and an outer periphery;
    a housing cover including a cavity within which the ring shape first lens is rotatable about the rotation axis, wherein the housing cover includes a second lens, and the cavity is defined by a bottom wall formed by the second lens, and first and second upright walls adjacent the respective inner periphery and outer periphery of the ring shape first lens;
    wherein the ring shape first lens and the second lens are in a light emitting path of the plurality of light emitting elements;
    wherein the ring shape first lens includes a boss that projects radially inwardly from the inner periphery of the ring shape first lens;
    a motion transfer member that is situated radially inwardly of the ring shape first lens and is configured to movably interact with the boss of the ring shape first lens to rotate the ring shape first lens about the rotation axis and within the cavity;
    wherein at least one of the inner periphery and the outer periphery of the ring shape first lens includes guide members configured to position the boss of the ring shape first lens to movably interact with the motion transfer member.

2. The light head of claim 1, further comprising a plurality of collimators in the light emitting path of the plurality of light emitting elements.

3. The light head of claim 1, wherein the guide members are configured to slidably contact a bearing surface of the housing cover.

4. The light head of claim 3, wherein the bearing surface of the housing cover guides the guide members of the ring shape first lens to guide the ring shape first lens in a concentric relationship with an annular shape outer cover of the housing cover.

5. The light head of claim 1, wherein the guide members include radially inward tabs that protrude from the inner periphery of the ring shape first lens and are configured to slidably contact a bearing surface of the housing cover.

6. The light head of claim 1, wherein the guide members include radially outward tabs that protrude from the outer periphery of the ring shape first lens and are configured to slidably contact a bearing surface of the housing cover.

7. The light head of claim 1, wherein the ring shape first lens and the boss are a single integral monolithic structure.

8. The light head of claim 1, wherein the ring shape first lens and the boss are a single integral molded component.

9. The light head of claim 1, wherein the rotation axis is at the center of the ring shape first lens.

10. The light head of claim 1, wherein the motion transfer member includes a lever.

11. The light head of claim 1, wherein the housing cover includes within the cavity thereof at least one of an inner periphery lower wall and an outer periphery lower wall, wherein the ring shape first lens and the housing cover are arranged so that the ring shape first lens is slidably movable on the at least one of the inner periphery lower wall and the outer periphery lower wall.

12. The light head of claim 11, wherein the housing cover and the at least one of the inner periphery lower wall and the outer periphery lower wall are a single integral molded component.

13. The light head of claim 1, wherein the housing cover includes a plurality of lens restricting members situated within the cavity of the housing cover and attached to one or more surfaces of the housing cover.

14. The light head of claim 13, wherein the ring shape first lens is radially restricted by bearing surfaces of the respective plurality of lens restricting members to rotationally guide the ring shape first lens about the rotation axis and within the cavity of the housing cover.

15. The light head of claim 13, wherein the ring shape first lens is axially restricted between bearing surfaces of the respective plurality of lens restricting members and bearing surfaces of the housing cover to rotationally guide the ring shape first lens about the rotation axis and within the cavity of the housing cover.

16. The light head of claim 13, wherein the plurality of lens restricting members are attached to the surface of the housing cover by fasteners.

17. A light head for a medical device support system, comprising:
    a housing base including a plurality of light emitting elements;
    an annular shape first lens that has a rotation axis;

a housing cover including a cavity within which the annular shape first lens is rotatable about the rotation axis, wherein the housing cover includes a second lens;

wherein the annular shape first lens and the second lens are in a light emitting path of the plurality of light emitting elements;

a driving source;

a lever that is movable relative to a fulcrum of the light head, wherein the lever includes a first end and a second end at opposite sides of the fulcrum, the first end spaced a first distance from the fulcrum, the second end spaced a second distance from the fulcrum;

wherein the lever is configured to transfer motion from the driving source at the first end thereof into rotational motion of the annular shape first lens about the rotation axis and within the cavity at the second end thereof in response to movement of the lever relative to the fulcrum based on the ratio of the first distance from the fulcrum to the second distance from the fulcrum.

18. The light head of claim 17, wherein the driving source includes a handle rotatably mounted coaxially to a hub of the light head, and the lever is configured to transfer rotational motion of the handle at the first end of the lever into rotational motion of the annular shape first lens at the second end of the lever.

19. The light head of claim 18, wherein the fulcrum includes a round shape fastener secured via a bracket to the hub.

20. The light head of claim 18, wherein the first end of the lever is movably coupled to a bushing of the handle.

21. The light head of claim 18, wherein the hub is secured to the housing cover.

22. The light head of claim 17, wherein the second end of the lever is movably coupled to the annular shape first lens.

23. The light head of claim 17, wherein the cavity has a predetermined depth and the entire lever is configured to move relative to the fulcrum within the depth of the cavity.

24. The light head of claim 17, wherein the first end, the fulcrum, and the second end are arranged at respective first, second, and third radial distances from the rotation axis, wherein the third radial distance is greater than the second radial distance, and the second radial distance is greater than the first radial distance.

25. A method of operating a light head of a medical device support system, comprising:
providing a light head including:
a housing base including a plurality of light emitting elements;
an annular shape first lens that has a ring shape and a rotation axis, the ring shape first lens having an inner periphery and an outer periphery;
a housing cover including a cavity within which the ring shape first lens is rotatable about the rotation axis, wherein the housing cover includes a second lens, and the cavity is defined by a bottom wall formed by the second lens, and first and second upright walls adjacent the respective inner periphery and outer periphery of the ring shape first lens;
wherein the ring shape first lens and the second lens are in a light emitting path of the plurality of light emitting elements;
wherein the ring shape first lens includes a boss that projects radially inwardly from the inner periphery of the ring shape first lens;
a motion transfer member that is situated radially inwardly of the ring shape first lens;

movably interacting the motion transfer member with the boss of the ring shape first lens to rotate the ring shape first lens about the rotation axis and within the cavity;
configuring guide members located at at least one of the inner periphery and the outer periphery of the ring shape first lens to position the boss of the ring shape first lens to movably interact with the motion transfer member.

26. A method of operating a light head of a medical device support system, comprising:
providing a light head including:
a housing base including a plurality of light emitting elements;
an annular shape first lens that has a rotation axis;
a housing cover including a cavity within which the annular shape first lens is rotatable about the rotation axis, wherein the housing cover includes a second lens;
wherein the annular shape first lens and the second lens are in a light emitting path of the plurality of light emitting elements;
a driving source;
moving a lever relative to a fulcrum of the light head, wherein the lever includes a first end and a second end at opposite sides of the fulcrum, the first end spaced a first distance from the fulcrum, the second end spaced a second distance from the fulcrum;
transferring motion from the driving source at the first end of the lever into rotational motion of the annular shape first lens about the rotation axis and within the cavity at the second end of the lever in response to movement of the lever relative to the fulcrum based on the ratio of the first distance from the fulcrum to the second distance from the fulcrum.

27. A light head for a medical device support system, comprising:
a housing base including a plurality of light emitting elements;
an annular shape first lens that has a rotation axis;
a housing cover including a cavity within which the annular shape first lens is rotatable about the rotation axis, wherein the housing cover includes a second lens;
wherein the annular shape first lens and the second lens are in a light emitting path of the plurality of light emitting elements;
a motion transfer member configured to movably interact with a boss of the annular shape first lens to rotate the annular shape first lens about the rotation axis and within the cavity,
wherein a periphery of the annular shape first lens includes guide members configured to position the boss of the annular shape first lens to movably interact with the motion transfer member;
the motion transfer member being movable relative to a fulcrum of the light head,
wherein the motion transfer member includes a first end and a second end at opposite sides of the fulcrum, the first end spaced a first distance from the fulcrum, the second end spaced a second distance from the fulcrum;
wherein the motion transfer member is configured to transfer motion from a driving source at the first end thereof into rotational motion of the annular shape first lens about the rotation axis and within the cavity at the second end thereof in response to movement of the motion transfer member relative to the fulcrum based on the ratio of the first distance from the fulcrum to the second distance from the fulcrum.

* * * * *